US012605139B2

(12) United States Patent
Bang et al.

(10) Patent No.: US 12,605,139 B2
(45) Date of Patent: Apr. 21, 2026

(54) METHOD OF IMPROVING QUALITY OF ULTRASOUND IMAGE AND ULTRASOUND IMAGING APPARATUS THEREFOR

(71) Applicant: Samsung Medison Co., Ltd., Gangwon-do (KR)

(72) Inventors: Minsuk Bang, Seoul (KR); Byungyeon Kim, Seoul (KR); Hanjun Kim, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 0 days.

(21) Appl. No.: 18/771,726

(22) Filed: Jul. 12, 2024

(65) Prior Publication Data

US 2025/0241618 A1     Jul. 31, 2025

(30) Foreign Application Priority Data

Jan. 29, 2024    (KR) ........................ 10-2024-0013400

(51) Int. Cl.
    *A61B 8/08*       (2006.01)
    *A61B 8/00*       (2006.01)
        (Continued)

(52) U.S. Cl.
    CPC .............. *A61B 8/0866* (2013.01); *A61B 8/10* (2013.01); *A61B 8/14* (2013.01); *A61B 8/465* (2013.01)

(58) Field of Classification Search
    CPC ........... A61B 8/0866; A61B 8/10; A61B 8/14; A61B 8/465
    See application file for complete search history.

(56) References Cited

U.S. PATENT DOCUMENTS

2016/0030007 A1    2/2016   Tsujita
2017/0251999 A1*   9/2017   Noguchi .................. A61B 8/13
               (Continued)

FOREIGN PATENT DOCUMENTS

KR    10-2016-0119307 A    10/2016
KR       10-2223753 B1     3/2021
               (Continued)

OTHER PUBLICATIONS

Feng et al. ;"Automatic Fetal Face Detection From Ultrasound Volumes via Learning 3D and 2D Information", IEEE, 2009; pp. 2488-2495 (Year: 2009).*
               (Continued)

*Primary Examiner* — Dixomara Vargas
(74) *Attorney, Agent, or Firm* — Morgan Lewis & Bockius LLP

(57) ABSTRACT

Provided is an ultrasound imaging apparatus and method of controlling the ultrasound imaging apparatus. The ultrasound imaging apparatus includes an ultrasound transceiver module, a display, an input interface, and at least one processor, wherein the at least one processor is configured to control the ultrasound transceiver module to transmit an ultrasound signal to a fetus and receive an ultrasound echo signal reflecting from the fetus, obtain ultrasound volume data of a face of the fetus based on the ultrasound echo signal, the ultrasound volume data including a lossy volume area where the ultrasound echo signal has a value equal to or less than a threshold value due to a strong reflector, display a two dimensional (2D) rendered image of the face of the fetus based on the ultrasound volume data and an ultrasound cross-sectional image of the face of the fetus through the display, the 2D rendered image including a lossy area not represented of the face of the fetus due to the lossy volume area, indicate an area to be restored among the lossy
               (Continued)

START

TRANSMIT ULTRASOUND SIGNAL TO FETUS AND RECEIVE ULTRASOUND ECHO SIGNAL REFLECTING FROM FETUS — S510

OBTAIN ULTRASOUND VOLUME DATA OF FACE OF FETUS BASED ON ULTRASOUND ECHO SIGNAL, THE ULTRASOUND VOLUME DATA INCLUDING LOSSY VOLUME AREA WHERE ULTRASOUND ECHO SIGNAL HAS THRESHOLD VALUE OR LESS DUE TO STRONG REFLECTOR — S520

DISPLAY 2D RENDERED IMAGE OF FACE OF FETUS AND ULTRASOUND CROSS-SECTIONAL IMAGE OF FACE OF FETUS BASED ON ULTRASOUND VOLUME DATA, THE 2D RENDERED IMAGE AND ULTRASOUND CROSS-SECTIONAL IMAGE INCLUDING LOSSY AREA NOT REPRESENTED OF FACE OF FETUS DUE TO LOSSY VOLUME AREA — S530

INDICATE AREA TO BE RESTORED AMONG LOSSY AREA ON 2D RENDERED IMAGE AND ULTRASOUND CROSS-SECTIONAL IMAGE — S540

RESTORE INDICATED AREA TO BE RESTORED BASED ON USER INPUT TO RESTORE AREA TO BE RESTORED BEING RECEIVED — S550

END area on the 2D rendered image or the cross-sectional image of the ultrasound volume data, and restore the indicated area to be restored based on a user input to restore the 2D rendered image or the ultrasound cross-sectional image of the ultrasound volume data being received through the input interface. The ultrasound imaging apparatus may display a location of a landmark of a face on a 2D rendered image of the face of a fetus, and clearly enhance the shape of the landmark at the location of the landmark.

20 Claims, 20 Drawing Sheets

(51) Int. Cl.
    *A61B 8/10*          (2006.01)
    *A61B 8/14*          (2006.01)

(56) References Cited

U.S. PATENT DOCUMENTS

| | | |
|---|---|---|
| 2018/0211391 A1 | 7/2018 | Prevost et al. |
| 2019/0259186 A1* | 8/2019 | Yoshida ................. A61B 8/483 |

| | | | |
|---|---|---|---|
| 2020/0178934 A1* | 6/2020 | Perrey ................. A61B 8/4254 |
| 2023/0102702 A1 | 3/2023 | Shin et al. | |
| 2024/0005589 A1* | 1/2024 | Maeda ................. G06T 7/0012 |
| 2025/0104226 A1* | 3/2025 | Kolmer ............... G06V 10/255 |

FOREIGN PATENT DOCUMENTS

| | | | |
|---|---|---|---|
| KR | 10-2021-0050830 A | 5/2021 | |
| KR | 10-2486300 B1 | 1/2023 | |
| WO | 2018/214063 A1 | 11/2018 | |
| WO | 2022/133806 A1 | 6/2022 | |

OTHER PUBLICATIONS

The Extended European Search Report dated Nov. 12, 2024 issued in European Patent Application No. 24186761.3.

European Notice of Allowance dated Feb. 23, 2026 issued in European Patent Application No. 24186761.3.

\* cited by examiner

FIG. 5

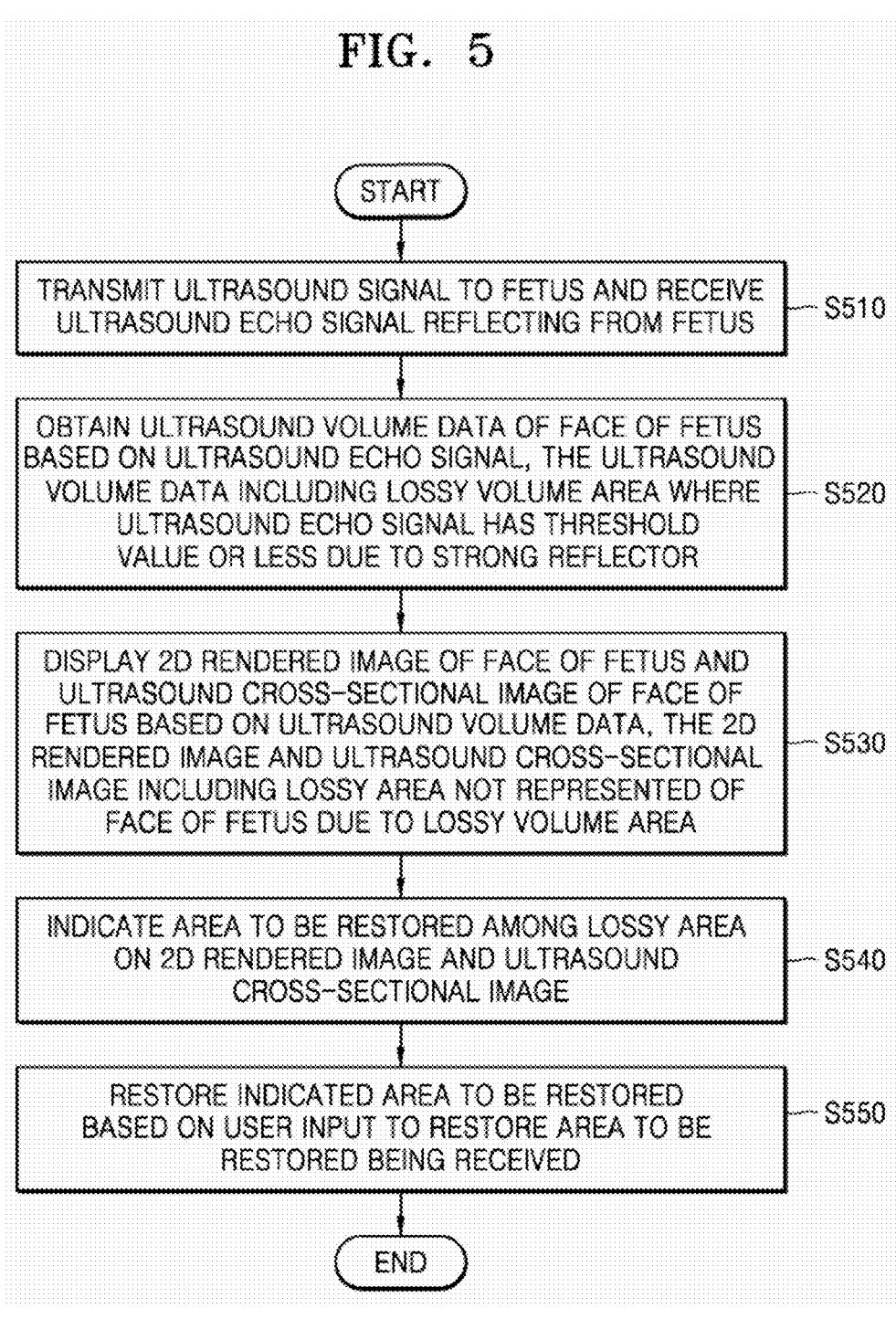

START

TRANSMIT ULTRASOUND SIGNAL TO FETUS AND RECEIVE ULTRASOUND ECHO SIGNAL REFLECTING FROM FETUS — S510

OBTAIN ULTRASOUND VOLUME DATA OF FACE OF FETUS BASED ON ULTRASOUND ECHO SIGNAL, THE ULTRASOUND VOLUME DATA INCLUDING LOSSY VOLUME AREA WHERE ULTRASOUND ECHO SIGNAL HAS THRESHOLD VALUE OR LESS DUE TO STRONG REFLECTOR — S520

DISPLAY 2D RENDERED IMAGE OF FACE OF FETUS AND ULTRASOUND CROSS-SECTIONAL IMAGE OF FACE OF FETUS BASED ON ULTRASOUND VOLUME DATA, THE 2D RENDERED IMAGE AND ULTRASOUND CROSS-SECTIONAL IMAGE INCLUDING LOSSY AREA NOT REPRESENTED OF FACE OF FETUS DUE TO LOSSY VOLUME AREA — S530

INDICATE AREA TO BE RESTORED AMONG LOSSY AREA ON 2D RENDERED IMAGE AND ULTRASOUND CROSS-SECTIONAL IMAGE — S540

RESTORE INDICATED AREA TO BE RESTORED BASED ON USER INPUT TO RESTORE AREA TO BE RESTORED BEING RECEIVED — S550

END

METHOD OF IMPROVING QUALITY OF ULTRASOUND IMAGE AND ULTRASOUND IMAGING APPARATUS THEREFOR

CROSS-REFERENCE TO RELATED APPLICATION

This application is based on and claims priority under 35 U.S.C. § 119 to Korean Patent Application No. 10-2024-0013400, filed on Jan. 29, 2024 in the Korean Intellectual Property Office, the disclosure of which is incorporated by reference herein in its entirety.

BACKGROUND

1. Field

The disclosure relates to an ultrasound imaging apparatus for improving quality of ultrasound images or rendered images based on ultrasound volume data, a method of controlling the ultrasound imaging apparatus, and a computer-readable recording medium having stored therein a computer program to perform the method of controlling the ultrasound imaging apparatus.

2. Description of the Related Art

In recent medical fields, many different types of medical imaging apparatuses are widely used to obtain information about biological tissues of the human body by imaging the information for the purpose of early diagnosis or operation of various diseases. As classic examples of these imaging apparatuses, there may be an ultrasound imaging apparatus, a computed tomography (CT) apparatus, and a magnetic resonance imaging (MRI) apparatus.

The ultrasound imaging apparatus is a device for non-invasively obtaining at least one image of an internal portion (e.g., a soft tissue or a blood flow) of an object by irradiating an ultrasound signal produced from a transducer of a probe to the object and receiving information of a signal reflecting from the object. The ultrasound imaging apparatus may be used for medical purposes such as observing inside of an object, detecting foreign substances, measuring injuries, etc. Such an ultrasound imaging apparatus is widely used along with other imaging devices as it has high stability, enables images to be displayed in real time and is free of radiation exposure thereby making it safe, as compared to the X-ray based imaging apparatus.

SUMMARY

Additional aspects will be set forth in part in the description which follows and, in part, will be apparent from the description, or may be learned by practice of the presented embodiments of the disclosure.

According to an embodiment, an ultrasound imaging apparatus is provided. The ultrasound imaging apparatus includes an ultrasound transceiver module, a display, an input interface, and at least one processor, wherein the at least one processor is configured to control the ultrasound transceiver module to transmit an ultrasound signal to a fetus and receive an ultrasound echo signal reflecting from the fetus, obtain ultrasound volume data of a face of the fetus based on the ultrasound echo signal, the ultrasound volume data including a lossy volume area where the ultrasound echo signal has a value equal to or less than a threshold value due to a strong reflector, display a two dimensional (2D)

rendered image of the face of the fetus based on the ultrasound volume data and an ultrasound cross-sectional image of the face of the fetus through the display, the 2D rendered image and the ultrasound cross-sectional image including a lossy area not represented of the face of the fetus due to the lossy volume area, indicate an area to be restored among the lossy area on the 2D rendered image, and restore the indicated area to be restored based on a user input to restore the 2D rendered image through the input interface.

According to an embodiment, a method of controlling an ultrasound imaging apparatus is provided. The method of controlling an ultrasound imaging apparatus includes transmitting an ultrasound signal to a fetus and receiving an ultrasound echo signal reflecting from the fetus, obtaining ultrasound volume data of a face of the fetus based on the ultrasound echo signal, displaying a 2D rendered image of the face of the fetus based on the ultrasound volume data, the 2D rendered image including a lossy area not represented of the face of the fetus, indicating an area to be restored in the lossy area on the 2D rendered image, and restoring the indicated area to be restored based on receiving a user input to restore the 2D rendered image.

According to an embodiment, a computer-readable recording medium having recorded thereon a program, when executed by a computer, to perform the method of controlling the ultrasound imaging apparatus.

BRIEF DESCRIPTION OF THE DRAWINGS

The disclosure may be readily understood by combinations of the following detailed descriptions and the accompanying drawings, and reference numerals refer to structural elements.

The above and other aspects, features, and advantages of certain embodiments of the disclosure will be more apparent from the following description taken in conjunction with the accompanying drawings, in which:

FIG. 5 illustrates a method by which an ultrasound imaging apparatus modifies a face of a fetus in a 2D rendered image, according to an embodiment;

DETAILED DESCRIPTION

Figure 1A:
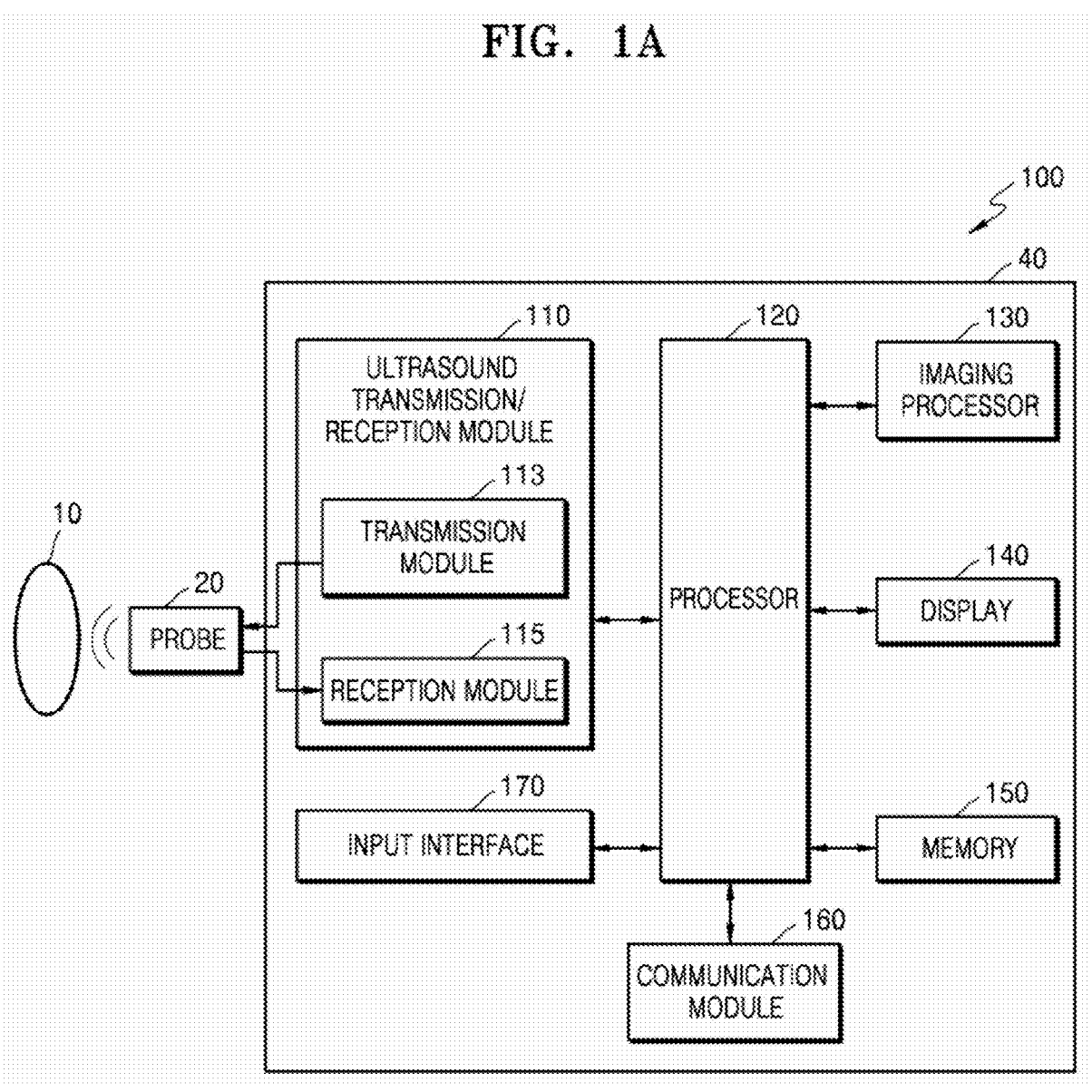
FIGS. 1A and 1B are block diagrams illustrating configurations of an ultrasound imaging system, according to an embodiment.

The disclosure describes principles of embodiments and describes the embodiments to clarify the scope of the appended claims of the disclosure and help those of ordinary skill in the art to which the embodiments belong practice the embodiments. The embodiments may be implemented in various forms.

Like numerals refer to like elements throughout the specification. Not all elements of embodiments of the disclosure will be described, and description of what are commonly known in the art or what overlap each other in the embodiments will be omitted. Throughout the specification, the term 'module' or 'unit' may refer to one implemented by at least one combination of software, hardware or firmware, and a plurality of modules or units may be implemented in one element or a single module or unit may include a plurality of elements depending on the embodiments.

The singular form of a noun corresponding to an item may include one or more items unless the context states otherwise.

In the disclosure, "A or B", "at least one of A and B", "at least one of A or B", "A, B or C", "at least one of A, B and C", and "at least one of A, B, or C" may each include any one or all the possible combinations of A, B and C.

The expression "and/or" is interpreted to include a combination or any of associated elements.

Terms like "first", "second", etc., may be simply used to distinguish an element from another, without limiting the elements in a certain sense (e.g., in terms of importance or order).

The terms 'front', 'rear', 'top', 'bottom', 'side', 'left', 'right', 'upper', 'lower', etc., as herein used are defined with respect to the drawings, but the terms may not restrict the shape and position of the respective components.

It will be further understood that the terms "comprise" and/or "comprising," when used in the disclosure, specify the presence of stated features, integers, steps, operations, elements, parts or combinations thereof, but do not preclude the possible presence or addition of one or more other features, integers, steps, operations, elements, components, and/or groups thereof.

When an element is mentioned as being "connected to", "coupled to", "supported on" or "contacting" another element, it includes not only a case that the elements are directly connected to, coupled to, supported on or contact each other but also a case that the elements are connected to, coupled to, supported on or contact each other through a third element.

Throughout the specification, when an element is mentioned as being located "on" another element, it implies not only that the element is abut on the other element but also that a third element exists between the two elements.

An ultrasound imaging apparatus according to various embodiments will now be described in detail in connection with the accompanying drawings. In describing embodiments with reference to accompanying drawings, like elements are given like reference numerals, in which case overlapping description will not be repeated.

In the disclosure, an image may include a medical image obtained by a medical imaging apparatus such as a magnetic resonance imaging (MRI) apparatus, a computed tomography (CT) apparatus, an ultrasound imaging apparatus or an X-ray imaging apparatus.

In the disclosure, the term 'object' refers to a target to be captured, including a human, an animal or a part thereof. For example, the object may include a part (e.g., organ) of the body or a phantom.

In the disclosure, the expression 'ultrasound image' refers to an image of an object generated or processed based on ultrasound signals transmitted to the object and then received from the object.

Embodiments of the disclosure will now be described in detail with reference to accompanying drawings.

Figure 1B:
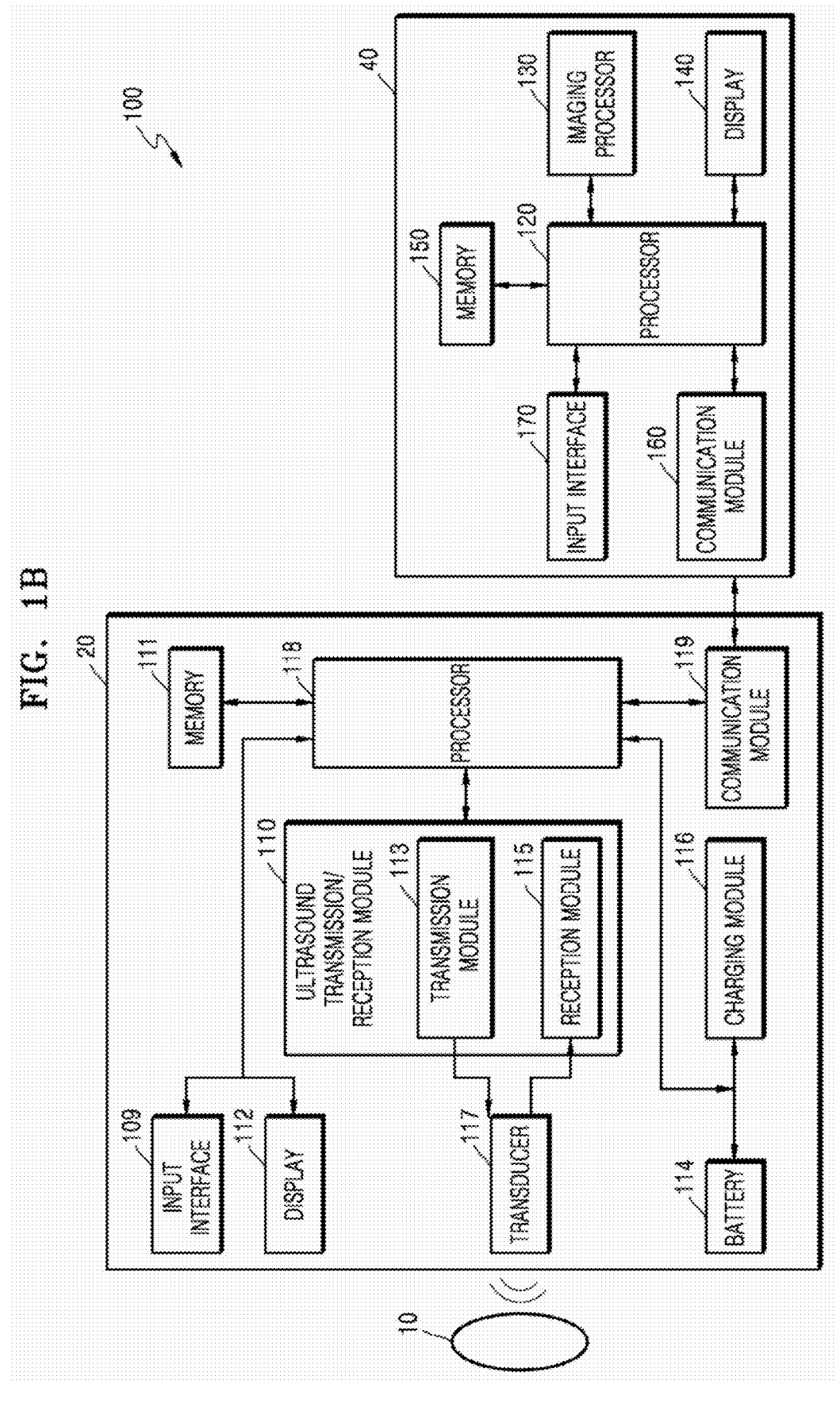

FIGS. 1A and 1B are block diagrams illustrating configurations of an ultrasound imaging system, according to an embodiment.

Referring to FIGS. 1A and 1B, an ultrasound imaging system 100 may include a probe 20 and an ultrasound imaging apparatus 40.

The ultrasound imaging apparatus 40 may be implemented in a cart type or a portable type. As an example of the portable-type ultrasound imaging apparatus, there may be, but not exclusively, a smart phone, a laptop computer, a personal digital assistant (PDA) or a tablet personal computer (PC), which includes a probe and an application. The ultrasound imaging device 40 may also be implemented in a probe-integrated type.

The probe 20 may include a wired probe wiredly connected to the ultrasound imaging apparatus 40 for wiredly communicating with the ultrasound imaging apparatus 40, a wireless probe wirelessly connected to the ultrasound imaging apparatus 40 for wirelessly communicating with the ultrasound imaging apparatus 40 and/or a hybrid probe wiredly or wirelessly connected to the ultrasound imaging apparatus 40 for wiredly or wirelessly communicating with the ultrasound imaging apparatus 40.

In various embodiments, the ultrasound imaging apparatus 40 may include an ultrasound transceiver module 110 as shown in FIG. 1A, or the probe 20 may include the ultrasound transceiver module 110 as shown in FIG. 1B. In various embodiments, it is also possible that both the ultrasound imaging apparatus 40 and the probe 20 include the ultrasound transceiver module 110.

In various embodiments, the probe 20 may include at least one or a combination of an image processor 130, a display 140 or an input interface 170. In the disclosure, descriptions of the ultrasound transceiver module 110, the image processor 130, the display 140 or the input interface 170 included in the ultrasound imaging apparatus 40 may be equally applied to the ultrasound transceiver module 110, the image processor 130, the display 140 or the input interface 170 included in the probe 20.

FIG. 1A is a block diagram illustrating a configuration of the ultrasound imaging system 100 with the probe 20 corresponding to a wired probe or a hybrid probe.

The probe 20 may include a plurality of transducers. The plurality of transducers may be arranged in a certain array and implemented as a transducer array. The transducer array may correspond to a one dimensional (1D) array or a two dimensional (2D) array. The plurality of transducers may transmit an ultrasound signal to an object 10 based on a transmission signal applied from a transmission module 113. The plurality of transducers may receive an ultrasound signal reflecting from the object 10, i.e., an ultrasound echo signal, to form a received signal. Furthermore, the probe 20 may be implemented integrally with the ultrasound imaging apparatus 40 or separated from but wiredly connected to the ultrasound imaging apparatus 40. Depending on implementations, the ultrasound imaging apparatus 40 may be connected to one or more probes 20.

When the probe 20 is a wired probe or a hybrid probe, it may include a cable and a connector to be connected to a connector of the ultrasound imaging apparatus 40.

In an embodiment, the probe 20 may be implemented as a 2D probe. When the probe 20 is implemented as the 2D probe, a plurality of transducers included in the probe 20 may be arrayed in 2D to form a 2D transducer array.

For example, the 2D transducer array may have a form in which a plurality of transducers are arranged in a first direction, forming a subarray, and a plurality of subarrays are arranged in a second direction that is different from the first direction.

Furthermore, in an embodiment, when the probe 20 is implemented as the 2D probe, the ultrasound transceiver module 110 may include at least one of an analog beamformer or a digital beamformer. In an embodiment, the 2D probe may include at least one or a combination of the analog beamformer or the digital beamformer, depending on the implementation.

The processor 120 controls the transmission module 113 to form a transmission signal to be applied to each transducer 115 by taking into account the locations and focus points of the plurality of transducers included in the probe 20.

The processor 120 may control a reception module 115 to generate ultrasound data by performing analog-to-digital conversion on the received signal received from the probe 20 and summing received signals which are converted into a digital form by taking into account the locations and focus points of the plurality of transducers.

When the probe 20 is implemented as the 2D probe, the processor 120 may calculate a time delay value for digital beamforming for each of the plurality of subarrays included in the 2D transducer array. The processor 120 may also calculate a time delay value for analog beamforming for each of the transducers included in one of the plurality of subarrays. The processor 120 may control the analog beamformer and the digital beamformer to form a transmission signal to be applied to each of the plurality of transducers based on the time delay values for analog beamforming and time delay values for digital beamforming. Furthermore, the processor 120 may control the analog beamformer to sum signals received from the plurality of transducers for each subarray based on the time delay values for analog beamforming. The processor 120 may also control the ultrasound transceiver module 110 to perform analog-to-digital conversion on the summed signal for each subarray. Furthermore, the processor 120 may control the digital beamformer to generate ultrasound data by summing the signals converted into a digital form based on the time delay values for digital beamforming.

The image processor 130 uses the generated ultrasound data to generate or process an ultrasound image.

The display 140 may display the generated ultrasound image, and various information processed by the ultrasound imaging apparatus 40 or the probe 20. The probe 20 or the ultrasound imaging apparatus 40 may include one or more displays 140 depending on the implementation. The display 140 may include a touch panel or a touch screen. Furthermore, the display 140 may include a flexible display.

The processor 120 may control general operation of the ultrasound imaging apparatus 40 and control operations of components of the ultrasound imaging apparatus 40. The processor 120 may execute a program or instructions stored in a memory or storage 150 to perform or control various operations or functions of the ultrasound imaging apparatus 40. Furthermore, the processor 120 may control the operation of the ultrasound imaging apparatus 40 by receiving a control signal from the input interface 170 or an external device.

The ultrasound imaging apparatus 40 may include a communication module 160 and may be connected through the communication module 160 to an external device (e.g., the probe 20, a server, a medical device or a portable device such as a smart phone, a tablet PC, a wearable device, etc.) for communication.

The communication module 160 may include one or more components that enable communication with the external device. The communication module 160 may include, for example, at least one of a short-range communication module, a wired communication module or a wireless communication module.

The communication module 160 may receive a control signal or data from the external device. The processor 120 may control operation of the ultrasound imaging apparatus 40 based on the control signal received through the communication module 160. The processor 120 may also control the external device based on a control signal by transmitting the control signal to the external device through the communication module 160. The external device may operate according to the control signal received from the ultrasound imaging apparatus 40 or process data received from the ultrasound imaging apparatus 40.

A program or application related to the ultrasound imaging apparatus 40 may be installed in the external device. The program or application installed in the external device may control the ultrasound imaging apparatus 40 or operate according to a control signal or data received from the ultrasound imaging apparatus 40.

The external device may receive or download the program or application related to the ultrasound imaging apparatus 40 from the ultrasound imaging apparatus 40, the probe 20 or a server, and install and run the program or application in the external device. The ultrasound imaging apparatus 40, the probe 20 or the server that provides the program or application may include a recording medium for storing instructions, commands, an installation file, an execution file or associated data of the program or application. The external device may be sold with the program or application installed therein.

The memory 150 may store various types of data or programs for operating and controlling the ultrasound imaging apparatus 40, input/output ultrasound data, ultrasound images, etc.

The input interface 170 may receive a user input to control the ultrasound imaging apparatus 40. For example, the user input may include, but not exclusively, an input of manipulating a button, a keypad, a mouse, a trackball, a jog switch, a knob, etc., an input of touching a touch pad or a touch screen, a voice input, a motion input, a biometric information input (e.g., of iris recognition, fingerprint recognition, etc.), etc.

The at least one processor 120 may control the ultrasound transceiver module 110 to transmit an ultrasound signal to the fetus and receive an ultrasound echo signal reflecting from the fetus.

The at least one processor 120 may obtain ultrasound volume data of a face of the fetus based on the ultrasound echo signal. In this case, the ultrasound volume data may include a lossy volume area where the ultrasound echo signal has a value equal to or less than a threshold value due to a strong reflector.

The at least one processor 120 may generate a 2D rendered image of the face of the fetus and an ultrasound cross-sectional image of the face of the fetus based on the ultrasound volume data. The ultrasound cross-sectional image of the face of the fetus may be, for example, an image comprised of cross-sectional data that represents the face of the fetus among the ultrasound volume data. In this case, the 2D rendered image and the ultrasound cross-sectional image may include a lossy area not represented of the face of the fetus due to the lossy volume area.

The at least one processor 120 may display the generated 2D rendered image and the ultrasound cross-sectional image through the display 140.

The at least one processor 120 may indicate an area to be restored in the lossy area on the 2D rendered image and the ultrasound cross-sectional image.

The at least one processor 120 may receive a user input to restore the area to be restored through the input interface 170.

The at least one processor 120 may restore the indicated area to be restored, based on the user input to restore the area to be restored.

The at least one processor 120 may determine a lossy volume area based on the ultrasound volume data and a direction in which the ultrasound signal is irradiated.

The at least one processor 120 may determine a lossy area in the 2D rendered image and the ultrasound cross-sectional image based on the lossy volume area.

The at least one processor 120 may indicate the lossy area determined in the 2D rendered image and the ultrasound cross-sectional image of the face of the fetus as an area to be restored through the display 140.

The at least one processor 120 may receive a user input to select an area to be restored on the ultrasound cross-sectional image through the input interface 170.

The at least one processor 120 may indicate an area selected on the ultrasound cross-sectional image and an area in the 2D rendered image corresponding to the selected area as an area to be restored, through the display 140.

The at least one processor 120 may receive a user input to select an area to be restored on the 2D rendered image of the face of the fetus, through the input interface 170. The at least one processor 120 may indicate the selected area to be restored on the 2D rendered image through the display 140. The at least one processor 120 may display an image indicating a location of an eye of the fetus at the location of the eye of the fetus in the 2D rendered image through the display 140.

Based on receiving a user input to enhance the 2D rendered image of the face of the fetus, the at least one processor 120 may clearly enhance the shape of the eye of the fetus at the location of the eye of the fetus.

The at least one processor 120 may determine a location of an eye of the fetus in the ultrasound volume data based on predetermined characteristics of eyes represented in the ultrasound volume data.

The at least one processor 120 may determine a location on the 2D rendered image corresponding to the determined location of the eye of the fetus as a location of the eye of the fetus in the 2D rendered image.

The at least one processor 120 may receive a user input to select an area of the eyes of the fetus on the ultrasound cross-sectional image through the input interface 170.

The at least one processor 120 may determine a location on the 2D rendered image corresponding to the selected location of the eye as a location of the eye of the fetus in the 2D rendered image.

The at least one processor 120 may receive a user input to select a location of an eye of the fetus on the 2D rendered image of the face of the fetus, through the input interface 170.

The at least one processor 120 may display both the 2D rendered image including the lossy area and the restored 2D rendered image through the display 140.

Figure 2A:
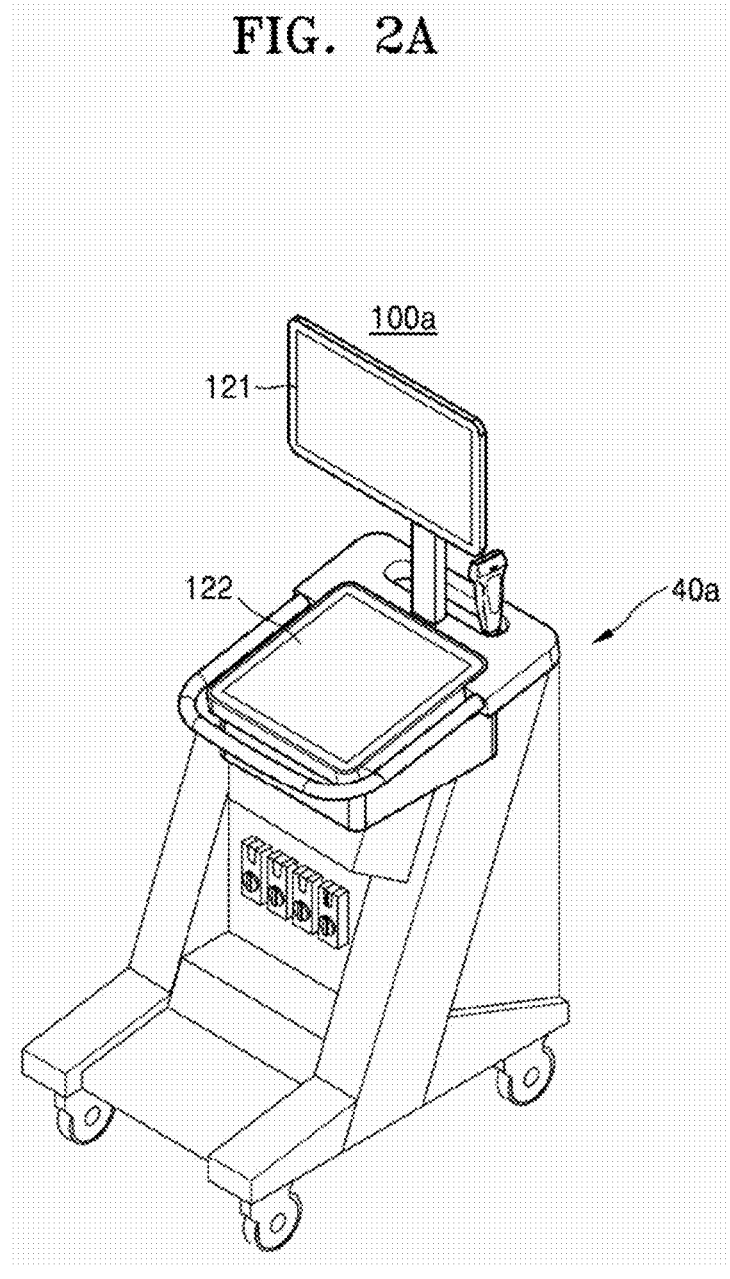
FIGS. 2A, 2B, 2C and 2D illustrate an ultrasound imaging system, according to an embodiment.
Figure 2B:
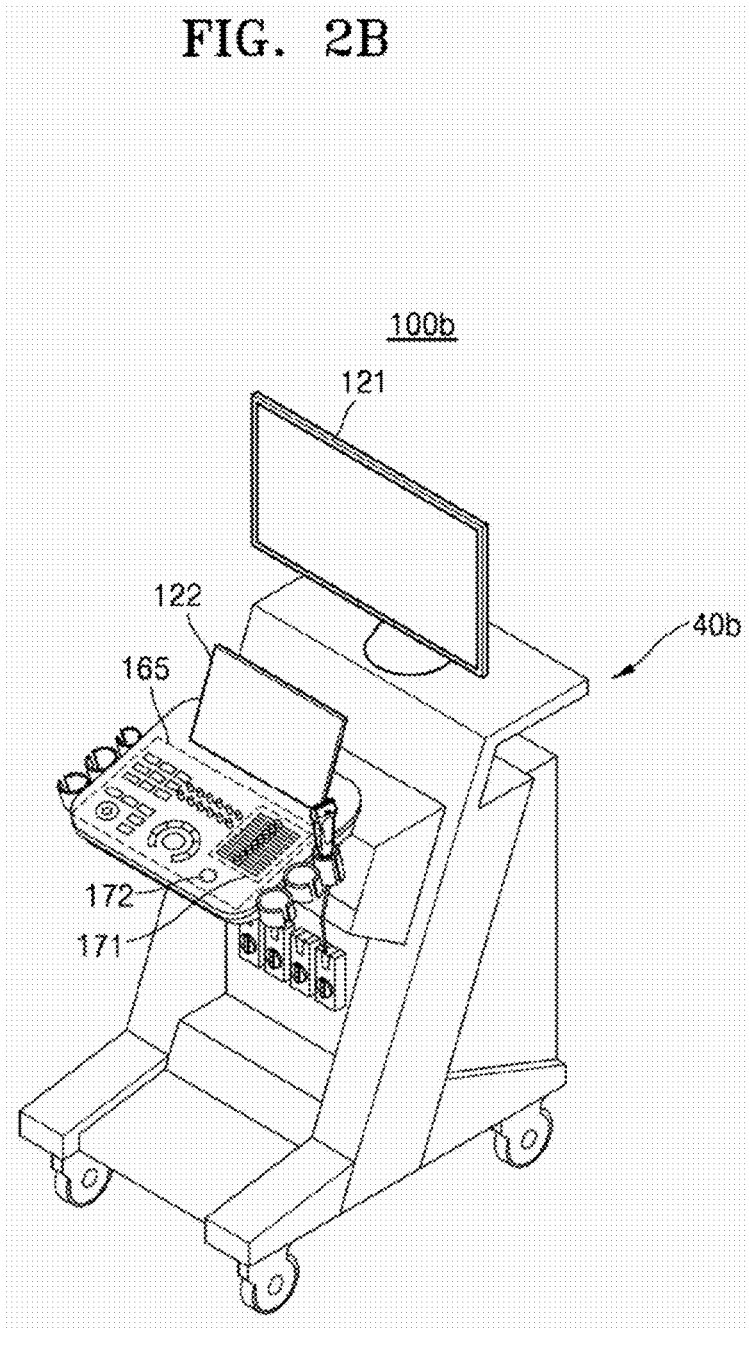

The display 140 may include a main display 121 (see FIGS. 2A and 2B) and a sub-display 122 (see FIGS. 2A and 2B).

The at least one processor 120 may display a plurality of 2D rendered images on the sub-display 122, the plurality of 2D rendered images having different enhancement levels and including the enhanced 2D rendered image.

On receiving a user input to select one of the plurality of 2D rendered images, the at least one processor 120 may display the selected 2D rendered image on the main display 121.

FIG. 1B is a control block diagram of the ultrasound imaging system 100 with the probe 20 corresponding to a wireless probe or a hybrid probe.

In various embodiments, it is obvious that the ultrasound imaging apparatus 40 shown in FIG. 1B may be replaced by the ultrasound imaging apparatus 40 as described above in connection with FIG. 1A.

In various embodiments, it is also obvious that the probe 20 shown in FIG. 1B may be replaced by the probe 20 as described above in connection with FIG. 1A.

The probe 20 may include a display 112, the transmission module 113, a battery 114, the transducer 117, a charging module 116, the reception module 115, an input interface 109, a processor 118 and a communication module 119. Although the probe 20 is shown in FIG. 1B as including both the transmission module 113 and the reception module 115, the probe 20 may include a portion of the configuration of the transmission module 113 and the reception module 115, or a portion of the configuration of the transmission module 113 and the reception module 115 may be included in the ultrasound imaging apparatus 40. In an embodiment, the probe 20 may further include the image processor 130.

The transducer 117 may be provided in the plural. The plurality of transducers may be arranged in a certain array and implemented as a transducer array. The transducer array may correspond to a 1D array or a 2D array. The plurality of transducers may transmit an ultrasound signal to the object 10 based on a transmission signal applied from the transmission module 113. The plurality of transducers may receive an ultrasound signal reflecting from the object 10 to form or generate an electric reception signal.

The charging module 116 may charge the battery 114. The charging module 116 may receive external power. In an embodiment of the disclosure, the charging module 116 may receive wireless power. Furthermore, in an embodiment, the charging module 116 may receive power wiredly. The charging module 116 may deliver the received power to the battery 114.

The processor 118 controls the transmission module 113 to generate or form a transmission signal to be applied to each of the plurality of transducers by taking into account the locations and focus points of the plurality of transducers.

The processor 118 controls the reception module 115 to generate ultrasound data by performing analog-to-digital conversion on the received signal received from the transducer 117 and summing the signals received and converted into a digital form by taking into account the locations and focus points of the plurality of transducers. In an embodiment, when the probe 20 includes the image processor 130, the generated ultrasound data may be used to generate an ultrasound image.

When the probe 20 is implemented as the 2D probe, the processor 118 may calculate a time delay value for digital beamforming for each of the plurality of subarrays included in the 2D transducer array. The processor 118 may also calculate a time delay value for analog beamforming for each of the transducers included in one of the plurality of subarrays. The processor 118 may control the analog beamformer and the digital beamformer to form a transmission signal to be applied to each of the plurality of transducers based on the time delay values for analog beamforming and time delay values for digital beamforming. Furthermore, the processor 118 may control the analog beamformer to sum signals received from the plurality of transducers for each subarray based on the time delay values for analog beamforming. The processor 118 may also control the ultrasound transceiver module 110 to perform analog-to-digital conversion on the summed signal for each subarray. Furthermore, the processor 118 may control the digital beamformer to generate ultrasound data by summing the signals converted to digital signals based on the time delay values for digital beamforming.

The processor 118 may control general operation of the probe 20 and control operations of the components of the probe 20. The processor 118 may execute a program or instructions stored in the memory 111 to perform or control various operations or functions of the probe 20. Furthermore, the processor 118 may receive a control signal from the input interface 109 of the probe 20 or an external device (e.g., the ultrasound imaging apparatus 40) to control an operation of the probe 20. Moreover, the processor 118 may receive a control signal from the input interface 109 or the external device to control an operation of the probe 20. The input interface 109 may receive a user input to control the probe 20. For example, the user input may include, but not exclusively, an input from manipulating a button, a keypad, a mouse, a trackball, a jog switch, a knob, etc., an input from touching a touch pad or a touch screen, a voice input, a motion input, a biometric information input (e.g., from iris recognition, fingerprint recognition, etc.), etc.

The display 112 may display an ultrasound image generated by the probe 20, an ultrasound image generated by processing the ultrasound data generated by the probe 20, an ultrasound image received from the ultrasound imaging apparatus 40 or various information processed by the ultrasound imaging system 100. The display 112 may further display status information of the probe 20. The status information of the probe 20 may include at least one of device information of the probe 20, battery state information of the probe 20, frequency band information of the probe 20, output information of the probe 20, information about whether there is an error in the probe 20, configuration information of the probe 20 or temperature information of the probe 20.

The probe 20 may include one or more displays 112 depending on the implementation. The display 112 may include a touch panel or a touch screen. Furthermore, the display 112 may include a flexible display.

The communication module 119 may wirelessly transmit the generated ultrasound data or ultrasound image to the ultrasound imaging apparatus 40 over a wireless network.

The communication module 119 may also receive a control signal and data from the ultrasound imaging apparatus 40.

The ultrasound imaging apparatus 40 may receive ultrasound data or an ultrasound image from the probe 20.

In an embodiment, when the probe 20 includes the image processor 130 that may use ultrasound data to generate an ultrasound image, the probe 20 may transmit the ultrasound data or the ultrasound image generated by the image processor 130 to the ultrasound imaging apparatus 40.

In an embodiment, when the probe 20 does not include the image processor 130 that may use the ultrasound data to generate an ultrasound image, the probe 20 may transmit the ultrasound data to the ultrasound imaging apparatus 40. The ultrasound data may include ultrasound raw data, and the ultrasound image may refer to ultrasound image data.

The ultrasound imaging apparatus 40 may include the processor 120, the image processor 130, the display 140, the memory 150, the communication module 160 and the input interface 170.

The image processor 130 uses the ultrasound data received from the probe 20 to generate or process an ultrasound image.

The display 140 may display an ultrasound image received from the probe 20, an ultrasound image generated by processing the ultrasound data received from the probe 20 or various information processed by the ultrasound imaging system 100. The ultrasound imaging apparatus 40 may include one or more displays 140 depending on the implementation. The display 140 may include a touch panel or a touch screen. Furthermore, the display 140 may include a flexible display.

The processor 120 may control general operation of the ultrasound imaging apparatus 40 and control operations of components of the ultrasound imaging apparatus 40. The processor 120 may execute a program or an application stored in the memory 150 to perform or control various operations or functions of the ultrasound imaging apparatus 40. Furthermore, the processor 120 may control the operation of the ultrasound imaging apparatus 40 by receiving a control signal from the input interface 170 or an external device.

The ultrasound imaging apparatus 40 may include the communication module 160 and may be connected through the communication module 160 to an external device (e.g., the probe 20, a server, a medical device or a portable device such as a smart phone, a tablet PC, a wearable device, etc.) for communication.

The communication module 160 may include one or more components that enable communication with the external device. The communication module 160 may include, for example, at least one of a short-range communication module, a wired communication module or a wireless communication module.

The communication module 160 of the ultrasound imaging apparatus 40 and the communication module 119 of the probe 20 may communicate with each other over a network or in a short-range wireless communication method. For example, the communication module 160 of the ultrasound imaging apparatus 40 and the communication module 119 of the probe 20 may communicate with each other by using one of wireless data communication schemes including a wireless local area network (WLAN), Wi-Fi, bluetooth, zigbee, WFD, infrared data association (IrDA), bluetooth low energy (BLE), near field communication (NFC), wireless broadband Internet (Wibro), world interoperability for microwave access (WiMAX), shared wireless access protocol (SWAP), wireless gigabit alliance (WiGig), radio frequency (RF) communication or 60 GHz millimeterwave (mmWave) short-range communication.

For this, the communication module 160 of the ultrasound imaging apparatus 40 and the communication module 119 of the probe 20 may include at least one of a WLAN communication module, a Wi-Fi communication module, a bluetooth communication module, a zigbee communication module, a WFD communication module, an IrDA communication module, a BLE communication module, an NFC communication module, a Wibro communication module, a WiMAX communication module, an SWAP communication module, a WiGig communication module, an RF communication module or a 60 GHz mmWave short-range communication module.

In an embodiment, the probe 20 may transmit device information (e.g., identity (ID) information) of the probe 20 to the ultrasound imaging apparatus 40 in a first communication method (e.g., BLE), and may be wirelessly paired with the ultrasound imaging apparatus 40. The probe 20 may also transmit ultrasound data and/or an ultrasound image to the paired ultrasound imaging apparatus 40.

The device information of the probe 20 may include various information relating to a serial number, a model name or a battery state of the probe 20.

The ultrasound imaging apparatus 40 may receive the device information (e.g., ID information) of the probe 20 from the probe 20 in the first communication method (e.g., BLE) and may be wirelessly paired with the probe 20. The ultrasound imaging apparatus 40 may also transmit an activation signal to the paired probe 20, and receive ultrasound data and/or an ultrasound image from the probe 20. The activation signal may include a signal to control an operation of the probe 20.

In an embodiment, the probe 20 may transmit device information (e.g., ID information) of the probe 20 to the ultrasound imaging apparatus 40 in a first communication method (e.g., BLE), and may be wirelessly paired with the ultrasound imaging apparatus 40. The probe 20 may transmit the ultrasound data and/or the ultrasound image to the ultrasound imaging apparatus 40 paired in the first communication method by using a second communication method (e.g., 60 GHz mmWave or Wi-Fi).

The ultrasound imaging apparatus 40 may receive the device information (e.g., ID information) of the probe 20 from the probe 20 in the first communication method (e.g., BLE) and may be wirelessly paired with the probe 20. The ultrasound imaging apparatus 40 may also transmit the activation signal to the paired probe 20, and receive the ultrasound data and/or the ultrasound image from the probe 20 in the second communication method (e.g., 60 GHz mmWave or Wi-Fi).

In an embodiment, the first communication method used for the probe 20 and the ultrasound imaging apparatus 40 to be paired with each other may have a lower frequency band than that of the second communication method used by the probe 20 to transmit the ultrasound data and/or the ultrasound image to the ultrasound imaging apparatus 40.

The display 140 of the ultrasound imaging apparatus 40 may display user interfaces (UIs) that represent device information of the probe 20. For example, the display 140 may display identification information of the wireless ultrasound probe 20, a paring method that represents a method of pairing with the probe 20, a data communication state between the probe 20 and the ultrasound imaging apparatus 40, a method of performing data communication with the ultrasound imaging apparatus 40, or a UI that indicates a battery state of the probe 20.

When the probe 20 includes the display 112, the display 112 of the probe 20 may display a UI that indicates device information of the probe 20. For example, the display 112 may display the identification information of the wireless ultrasound probe 20, the paring method that represents a method of pairing with the probe 20, the data communication state between the probe 20 and the ultrasound imaging apparatus 40, the method of performing data communication with the ultrasound imaging apparatus 40, or the UI that indicates a battery state of the probe 20.

The communication module 160 may receive a control signal or data from the external device. The processor 120 may control operation of the ultrasound imaging apparatus 40 based on the control signal received through the communication module 160.

The processor 120 may also control the external device based on a control signal by transmitting the control signal to the external device through the communication module 160. The external device may operate according to the control signal received from the ultrasound imaging apparatus 40 or process data received from the ultrasound imaging apparatus 40.

The external device may receive or download the program or application related to the ultrasound imaging apparatus 40 from the ultrasound imaging apparatus 40, the probe 20 or a server, and install and run the program or application in the external device. The ultrasound imaging apparatus 40, the probe 20 or the server that provides the program or application may include a recording medium for storing instructions, commands, an installation file, an execution file or associated data of the program or application. The external device may be sold with the program or application installed therein.

The memory 150 may store various types of data or programs, input/output ultrasound data, ultrasound images, etc., for operating and controlling the ultrasound imaging apparatus 40.

Examples of the ultrasound imaging system 100 according to an embodiment will now be described in connection with FIGS. 2A, 2B, 2C and 2D.

FIGS. 2A, 2B, 2C and 2D illustrate an ultrasound imaging apparatus, according to an embodiment.

Referring to FIGS. 2A and 2B, ultrasound imaging apparatuses 40a and 40b may include a main display 121 and a sub-display 122. The main display 121 and the sub-display 122 may correspond to the display 140 of FIGS. 1A and 1B. At least one of the main display 121 or the sub-display 122 may be implemented as a touch screen. The at least one of the main display 121 or the sub-display 122 may display an ultrasound image or various information processed by the ultrasound imaging apparatus 40a or 40b. Furthermore, the at least one of the main display 121 or the sub-display 122 may be implemented as a touch screen, and may receive data to control the ultrasound imaging apparatus 40a or 40b from the user by providing a graphic user interface (GUI). For example, the main display 121 may display an ultrasound image, and the sub-display 122 may display a control panel for controlling the displaying of the ultrasound image in a GUI form. The sub-display 122 may receive data to control displaying of the image through the control panel displayed in the form of the GUI. For example, a time grain compensation (TGC) button, a lateral gain compensation (LGC) button, a freeze button, a trackball, a jog switch or a knob may be provided as GUIs on the sub-display 122.

The ultrasound imaging apparatus 40a or 40b may use the input control data to control displaying of the ultrasound image displayed on the main display 121. Furthermore, the ultrasound imaging apparatus 40a or 40b may be wiredly or wirelessly connected to the probe 20 to transmit or receive an ultrasound signal to or from the object.

Referring to FIG. 2B, the ultrasound imaging apparatus 40b may further include a control panel 165 in addition to the main display 121 and the sub-display 122. The control panel 165 may include a button, a trackball, a jog switch, a knob, etc., and may receive data to control the ultrasound imaging apparatus 40b from the user. For example, the control panel 165 may include a TGC button 171, a freeze button 172, etc. The TGC button 171 is a button for setting a TGC value for each depth of the ultrasound image. Furthermore, when detecting an input to the freeze button 172 is detected while scanning the ultrasound image, the ultrasound imaging apparatus 40b may keep displaying a frame image at the moment, capture the frame image at the moment, or store the frame image at the moment.

In the meantime, the button, the trackball, the jog switch, the knob, etc., included in the control panel 165 may be provided as GUIs on the main display 121 or the sub-display 122. The ultrasound imaging apparatus 40a or 40b may be connected to the probe 20 to transmit or receive an ultrasound signal to or from the object.

The ultrasound imaging apparatus 40a or 40b may include various types of input/output interfaces such as a speaker, a light emitting diode (LED), a vibration device, etc. For example, the ultrasound imaging apparatus 40a or 40b may output various information through the input/output interface in such a form as graphics, sound or vibration. The ultrasound imaging apparatus 40a or 40b may output various types of notifications or data through the input/output interface.

Figure 2C:
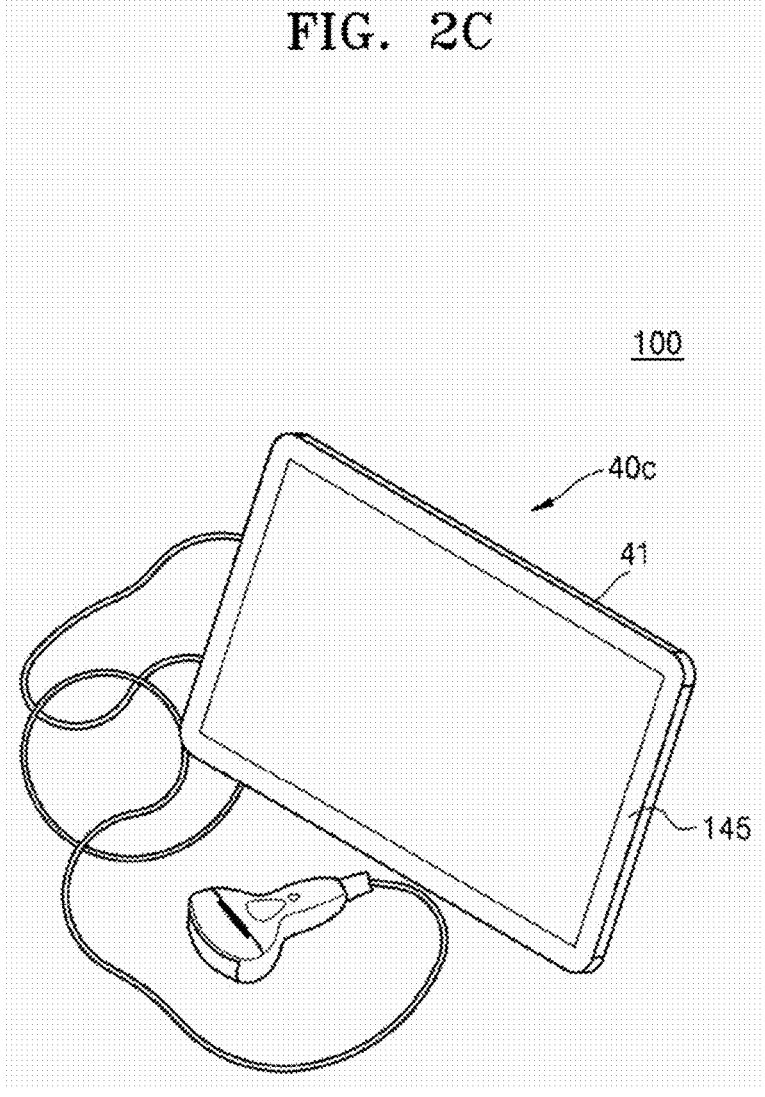
Figure 2D:
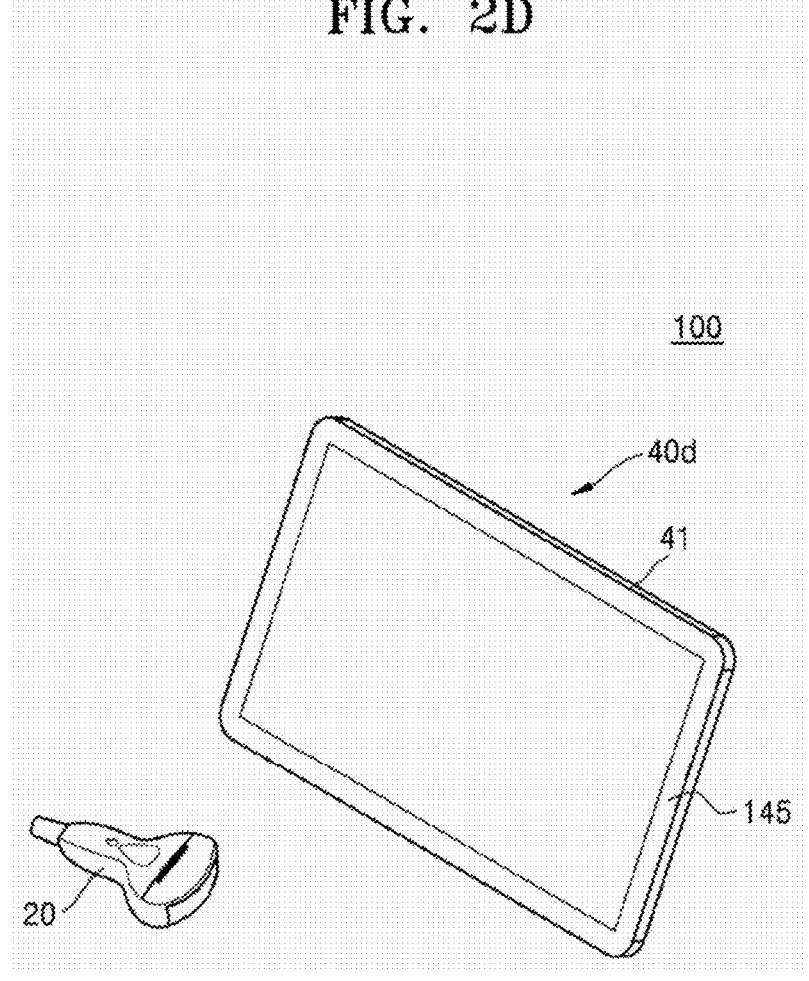

Referring to FIGS. 2C and 2D, ultrasound imaging apparatuses 40c and 40d may be implemented in a portable type. As an example of the portable-type ultrasound imaging apparatuses 40c and 40d, there may be, but not exclusively, a smart phone, a laptop computer, a PDA or a tablet PC, which includes a probe and an application.

The ultrasound imaging apparatus 40c may include a main body 411. Referring to FIG. 2C, the probe 20 may be wiredly connected to a side of the main body 41. For this, the main body 41 may include a connection terminal, to or from which a cable connected to the probe 20 may be attached or detached. The probe 20 may include the cable that includes a connection terminal to be connected to the main body 41.

Referring to FIG. 2D, the probe 20 may be wirelessly connected to the ultrasound imaging apparatus 40d. The main body 41 may include an input/output interface (e.g., a touch screen). The input/output interface may display an ultrasound image, various information processed by the ultrasound imaging apparatus 40d or a GUI.

The ultrasound imaging apparatus 40d and the probe 20 may establish communication or may be paired by a short-range wireless communication. For example, the ultrasound imaging apparatus 40d and the probe 20 may use bluetooth, BLE, Wi-Fi or Wi-Fi direct to communicate with each other.

The ultrasound imaging apparatus 40c or 40d may run a program or application related to the probe 20 to control the probe 20 and output information relating to the probe 20. The ultrasound imaging apparatus 40c or 40d may perform an operation related to the probe 20 while communicating with a certain server. The probe 20 may be registered in the ultrasound imaging apparatus 40c or 40d or in the certain server. The ultrasound imaging apparatus 40c or 40d may communicate with the registered probe 20 and perform an operation related to the probe 20.

Furthermore, the ultrasound imaging apparatus 40c or 40d may include various types of input/output interfaces such as a speaker, an LED, a vibration device, etc. For example, the ultrasound imaging apparatus 40c or 40d may output various information through the input/output interface in such a form as graphics, sound or vibration. The ultrasound imaging apparatus 40c or 40d may output various types of notifications or data through the input/output interface.

In an embodiment, the ultrasound imaging apparatus 40a, 40b, 40c or 40d may use an artificial intelligence (AI) model to process the ultrasound image or obtain additional information from the ultrasound image. In an embodiment, the ultrasound imaging apparatus 40a, 40b, 40c or 40d may use the AI model to generate an ultrasound image or perform such a process as correction, image quality enhancement, encoding or decoding on the ultrasound image. Furthermore, in an embodiment, the ultrasound imaging apparatus 40a, 40b, 40c or 40d may use the AI model to perform a process such as defining a baseline, obtaining anatomical information, obtaining lesion information, extracting a surface, defining boundary, measuring a length, measuring an area, measuring a volume or generating an annotation from the ultrasound image.

The AI model may be equipped in the ultrasound imaging apparatus 40a, 40b, 40c or 40d or in a server.

The AI model may be implemented by using various artificial neural networks or deep neural networks. The AI model may be trained or generated by using various machine learning algorithms or deep learning algorithms. The AI model may be implemented by using a model, such as a convolutional neural network (CNN), a recurrent neural network (RNN), a generative adversarial network (GAN), long short-term memory (LSTM), etc.

Figure 3:
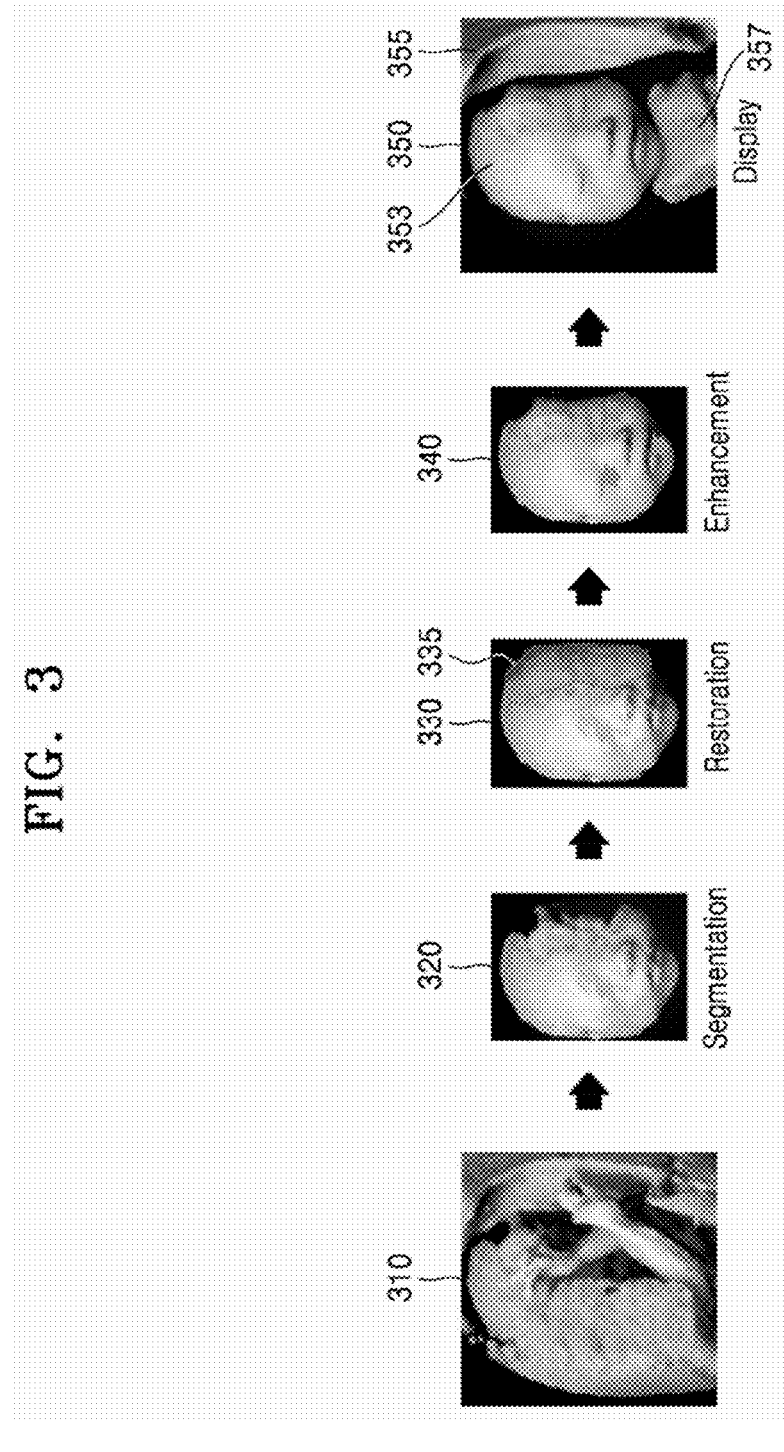
FIG. 3 illustrates a method by which an ultrasound imaging apparatus restores and enhances a two-dimensional (2D) rendered image of a fetus, according to an embodiment.

FIG. 3 illustrates a method by which the ultrasound imaging apparatus 40 restores and enhances a 2D rendered image of a fetus, according to an embodiment.

Referring to FIG. 3, the ultrasound imaging apparatus 40 may modify an image of a face of a fetus more perfectly and clearly by segmenting, restoring and enhancing a 2D rendered image of the fetus.

The ultrasound imaging apparatus 40 may obtain ultrasound volume data of the fetus based on an ultrasound echo signal received from the fetus. For example, the ultrasound imaging apparatus 40 may transmit an ultrasound signal to a cross-section of the fetus and receive an ultrasound echo signal from the cross-section. For example, the ultrasound imaging apparatus 40 may transmit ultrasound signals to adjacent cross-sections and receive ultrasound echo signals therefrom. The ultrasound imaging apparatus 40 may obtain ultrasound volume data based on the received ultrasound echo signals. For example, the ultrasound volume data may include a three dimensional (3D) location and a data value at the 3D location. Accordingly, 3D volume data that represents the fetus may be formed. A 3D spatial point in the ultrasound volume data may be referred to as a voxel.

The ultrasound imaging apparatus 40 may obtain a 2D rendered image 310 of the fetus based on the obtained ultrasound volume data. For example, the ultrasound imaging apparatus 40 may determine a location of the face of the fetus from the ultrasound volume data, and render the face of the fetus in a viewing direction to obtain the 2D rendered image 310 of the fetus.

Rendering the 3D ultrasound volume data into the 2D rendered image may be performed in one of the methods used in the imaging technology fields.

The 2D rendered image 310 of the fetus may include not only the head including the face of the fetus but also the hands and the uterine wall, as shown in FIG. 3.

The ultrasound imaging apparatus 40 may segment the face of the fetus on the 2D rendered image 310 of the fetus. For example, the ultrasound imaging apparatus 40 may obtain ultrasound volume data of the head of the fetus from the ultrasound volume data of the fetus. The ultrasound imaging apparatus 40 may display a 2D rendered image 320 of the head of the fetus by rendering the ultrasound volume data of the head of the fetus. The 2D rendered image 320 of the head of the fetus may be an image rendered in a direction in which the face of the fetus is viewed.

The 2D rendered image 320 of the head of the fetus may include a lossy area not represented of the face of the fetus. For example, when the ultrasound signal transmitted to the fetus meets a strong reflector (e.g., hand bones of the fetus), it may not pass through the strong reflector. Hence, the ultrasound signal may be hardly delivered to an area beyond the strong reflector in the transmitting direction of the ultrasound signal. In this case, for the area to which the ultrasound signal fails to be delivered due to the strong reflector, the data value may appear to be equal to or less than a threshold value in the ultrasound volume data. In an embodiment, the area to which the ultrasound signal fails to be delivered normally due to the strong reflector may be referred to as a lossy volume area. When the lossy volume area is rendered in a 2D image, it may appear as a lossy area where a portion of the face of the fetus is not represented as in the second 2D rendered image 320 of FIG. 3.

The ultrasound imaging apparatus 40 may restore the lossy area not represented of the face of the fetus. For example, the ultrasound imaging apparatus 40 may restore the lossy area by using face symmetry. The ultrasound imaging apparatus 40 may determine a median plane of the ultrasound volume data, and obtain a data value of the lossy volume area based on data of a volume area symmetrical to the lossy volume area of the ultrasound volume data with respect to the median plane. The ultrasound imaging apparatus 40 may display a 2D rendering image 330 with the lossy area restored by rendering the ultrasound volume data including the data value obtained of the lossy volume area. In an embodiment, the ultrasound imaging apparatus 40 may display an image 335 that represents the restored area on the 2D rendered image 330 with the lossy area restored.

The ultrasound imaging apparatus 40 may enhance the face of the fetus more clearly. For example, the ultrasound imaging apparatus 40 may enhance landmarks (e.g., eyes, nose, and mouth) of the face more clearly in the 2D rendered image 330. Furthermore, the ultrasound imaging apparatus 40 may modify the skin of the fetus more smoothly in the 2D rendered image 330. Locations of the eyes, nose and mouth of the fetus may be selected by the user, or automatically identified based on the ultrasound volume data.

For example, the ultrasound imaging apparatus 40 may identify a location of an eye of the fetus in the ultrasound volume data, and determine a location on the 2D rendered image corresponding to the identified location of the eye as a location of the eye of the fetus on the 2D rendered image. Furthermore, the ultrasound imaging apparatus 40 may display a 2D rendered image 340 with the eyes of the fetus enhanced more clearly by modifying shape and contrast of the eyes at the locations of the eyes of the fetus in the 2D rendered image.

The ultrasound imaging apparatus 40 may display a restored and enhanced 2D rendered image 350. In an embodiment, the 2D rendered image 350 of the fetus may include not only a restored and enhanced face image 353 of the fetus, but also a uterine wall image 355 and a body image 357 of the fetus.

It may be difficult to clearly represent an unclear portion of the face of the fetus only with the 2D rendered image itself. The ultrasound imaging apparatus 40 may use the ultrasound volume data to restore the lossy area and clearly enhance the landmarks of the face to more closely resemble the actual face of the fetus.

In an embodiment, on receiving a user input to display the facial image of the fetus after the 2D rendered image 310 of the fetus is displayed, the ultrasound imaging apparatus 40 may automatically perform an operation of segmenting the face of the fetus on the 2D rendered image 310 of the fetus, an operation of restoring the lossy area and an operation of clearly enhancing the landmark of the face, and display the modified face 353 of the fetus. Furthermore, on receiving a user input to re-modify the face of the fetus after the modified face 353 of the fetus is displayed, the ultrasound imaging apparatus 40 may provide a user interface for restoring the face of the fetus (e.g., a user interface for selecting a restoration area) or provide a user interface for enhancing the face of the fetus (e.g., a user interface for selecting a landmark of the face).

In an embodiment, the ultrasound imaging apparatus 40 may display the 2D rendered image 310 of the fetus, and on receiving a user input to display the facial image of the fetus, perform at least one of an operation of segmenting the face of the fetus from the 2D rendered image 310 of the fetus, an operation of restoring the lossy area, or an operation of clearly enhancing the landmark of the face, and display the modified face 353 of the fetus. In other words, at least one of the operation of segmenting the face of the fetus from the 2D rendered image 310, the operation of restoring the lossy area, or the operation of clearly enhancing the landmark of the face may be omitted.

Figure 4:
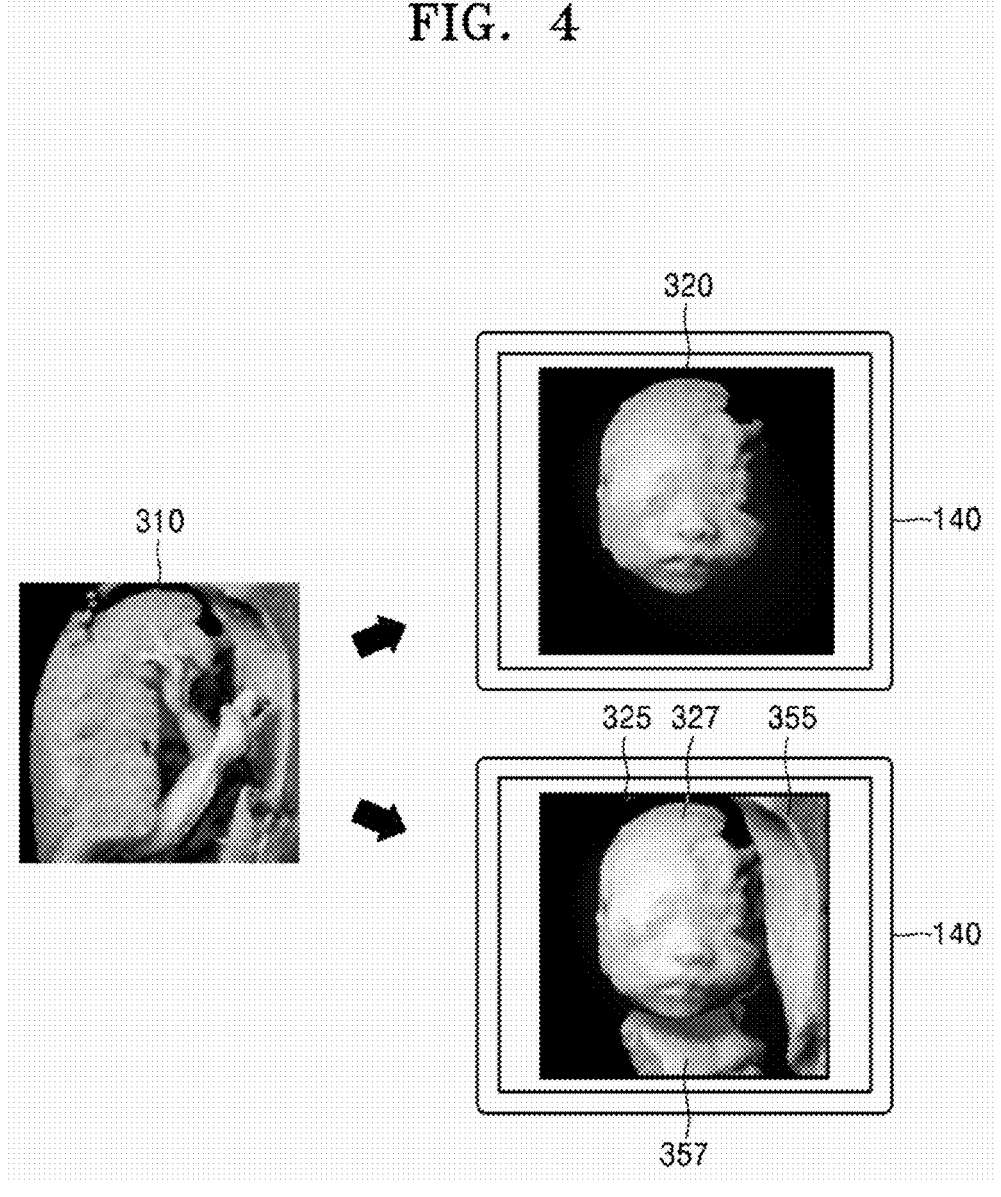
FIG. 4 illustrates a method by which an ultrasound imaging apparatus segments and displays a 2D rendered image of a fetus on receiving a user input to display a face of the fetus, according to an embodiment.

FIG. 4 illustrates a method by which the ultrasound imaging apparatus 40 segments and displays a 2D rendered image of a fetus on receiving a user input to display a face of the fetus, according to an embodiment.

Referring to FIG. 4, the ultrasound imaging apparatus 40 may receive an ultrasound echo signal from the fetus and display the 2D rendered image 310 of the fetus based on ultrasound volume data obtained from the ultrasound echo signal.

In a case that the ultrasound volume data obtained from the ultrasound echo signal is rendered as it is, the 2D rendered image 310 may include not only a main structure (e.g., the face of the fetus) in which the user is interested but also surrounding structures such as the fetus's body, hands, feet and a uterine wall.

Hence, the surrounding structures may make it difficult to identify the main structure which requires image enhancement.

In an embodiment, the ultrasound imaging apparatus 40 may display only the main structure without the surrounding structures for the user to get easy access to the main structure. For example, on receiving a user input to display the face of the fetus in the 2D rendered image 310, the ultrasound imaging apparatus 40 may display the 2D rendered image 320 on the display 140, which includes only the face without the body, hands, feet and the uterine wall. The user input to display the face of the fetus in the 2D rendered image 310 may include, for example, a user input to select a menu for displaying the face of the fetus.

In an embodiment, the ultrasound imaging apparatus 40 may display the main structure along with a structure that does not obstruct the main structure. For example, on receiving a user input to display the face of the fetus in the 2D rendered image 310, the ultrasound imaging apparatus 40 may display the 2D rendered image 325 on the display 140, which includes a body 357 and a uterine wall 355 with a face 327.

In an embodiment, the ultrasound imaging apparatus 40 may provide a user interface for selecting a structure to be excluded. For example, the ultrasound imaging apparatus 40 may delete the structure selected by the user from the 2D rendered image 310, and display a 2D rendered image with the selected structure deleted therefrom.

FIG. 5 illustrates a method by which the ultrasound imaging apparatus 40 modifies a face of a fetus in a 2D rendered image, according to an embodiment.

In operation S510, the ultrasound imaging apparatus 40 may transmit an ultrasound signal to a fetus and receive an ultrasound echo signal reflecting from the fetus.

For example, the ultrasound imaging apparatus 40 may use, but not exclusively, a phased probe, a linear probe or a convex probe to transmit the ultrasound signal to the fetus and receive the ultrasound echo signal reflecting from the fetus.

In operation S520, the ultrasound imaging apparatus 40 may obtain ultrasound volume data of the face of the fetus based on the ultrasound echo signal, and the ultrasound volume data may include a lossy volume area in which the ultrasound echo signal has a threshold value or less due to a strong reflector.

The ultrasound volume data may refer to reconstructed data in a 3D form obtained from accumulation of cross-sectional images of a certain area of the object.

The ultrasound volume data obtained from the ultrasound echo signal may have a form that varies by the type of the probe in use. For example, when the phased probe is used, the ultrasound volume data may have the form of a quadrangular pyramid having a base plane shaped like a curved right quadrangle. When the linear probe is used, the ultrasound volume data may have the form of a rectangular parallelepiped.

The ultrasound imaging apparatus 40 may obtain ultrasound volume data of the fetus based on the ultrasound echo signal. The ultrasound volume data of the fetus may include a face of the fetus.

The ultrasound signal may be hardly delivered to an area beyond the strong reflector in the transmitting direction of the ultrasound signal. In this case, for the area to which the ultrasound signal fails to be delivered due to the strong reflector, the data value may appear to be equal to or less than a threshold value in the ultrasound volume data. The area having a data value equal to or less than the threshold value in the ultrasound volume data due to the strong reflector may be referred to as a lossy volume area.

In operation S530, the ultrasound imaging apparatus 40 may display a 2D rendered image of the face of the fetus and an ultrasound cross-sectional image of the face of the fetus based on the ultrasound volume data, and the 2D rendered image and the ultrasound cross-sectional image may include a lossy area not represented of the face of the fetus due to the lossy volume area.

The ultrasound imaging apparatus 40 may determine a direction that views the face of the fetus in the ultrasound volume data from a viewpoint of a virtual viewer. The ultrasound imaging apparatus 40 may generate a 2D rendered image by rendering the ultrasound volume data based on the determined viewpoint.

The generating of the 2D rendered image by rendering the ultrasound volume data may be performed by using one of the existing volume rendering methods known to the public. For example, the ultrasound imaging apparatus 40 may perform volume rendering on the ultrasound volume data by ray casting.

In an embodiment, the ultrasound cross-sectional image may be a cross-sectional image of the ultrasound volume data, which represents the face of the fetus of the ultrasound volume data. In an embodiment, the ultrasound imaging apparatus 40 may display a volume image in which at least a portion of the ultrasound volume data is represented in 3D coordinates instead of the ultrasound cross-sectional image.

When the lossy volume area, to which the ultrasound signal is not delivered due to the strong reflector, is rendered into a 2D image, it may appear as the lossy area where a portion of the face of the fetus is not represented. Due to the lossy volume area, even in the ultrasound cross-sectional image that represents the face of the fetus of the ultrasound volume data, a lossy area where a portion of the face of the fetus is not represented may appear.

In operation S540, the ultrasound imaging apparatus 40 may display an area to be restored in the lossy area on the 2D rendered image and the ultrasound cross-sectional image.

In an embodiment, the ultrasound imaging apparatus 40 may identify the lossy volume area based on the ultrasound volume data. The ultrasound imaging apparatus 40 may determine a lossy area in the 2D rendered image and the ultrasound cross-sectional image based on the lossy volume area. The ultrasound imaging apparatus 40 may indicate the determined lossy area on the 2D rendered image and the ultrasound cross-sectional image as an area to be restored.

In an embodiment, the ultrasound imaging apparatus 40 may receive a user input to select an area on the displayed ultrasound cross-sectional image. The ultrasound imaging apparatus 40 may display, on the 2D rendered image, the selected area and an area in the 2D rendered image corresponding to the selected area as the area to be restored.

In an embodiment, the ultrasound imaging apparatus 40 may receive a user input to directly select an area to be restored on the 2D rendered image of the face of the fetus.

In operation S550, the ultrasound imaging apparatus 40 may restore the displayed area based on a user input to restore the area to be restored being received.

For example, the ultrasound imaging apparatus 40 may restore the area displayed as an area to be restored based on face symmetry and the ultrasound volume data.

In an embodiment, the ultrasound imaging apparatus 40 may display both the 2D rendered image including the lossy area and the restored 2D rendered image.

In an embodiment, the ultrasound imaging apparatus 40 may determine a location of a landmark of the face on the 2D rendered image, and clearly enhance the landmark of the face at the determined location.

In an embodiment, the ultrasound imaging apparatus 40 may determine locations of the eyes of the fetus in the ultrasound volume data, and determine locations on the 2D rendered image corresponding to the determined locations of the eyes of the fetus as locations of the eyes of the fetus on the 2D rendered image. The ultrasound imaging apparatus 40 may clearly enhance the shape of the eyes of the fetus at the determined locations of the eyes of the fetus.

In an embodiment, the ultrasound imaging apparatus 40 may receive a user input to select areas of the eyes of the fetus on the ultrasound cross-sectional image, and determine locations in the 2D rendered image corresponding to the selected areas of the eyes as locations of the eyes of the fetus in the 2D rendered image. The ultrasound imaging apparatus 40 may clearly enhance the shape of the eyes of the fetus at the determined locations of the eyes of the fetus.

In an embodiment, the ultrasound imaging apparatus 40 may receive a user input to directly select locations of the eyes of the fetus on the 2D rendered image of the face of the fetus, and clearly enhance the shape of the eyes of the fetus at the selected locations of the eyes of the fetus.

Furthermore, on receiving a user input that selects an enhancement level, the ultrasound imaging apparatus 40 may display a 2D rendered image corresponding to the selected enhancement level.

Figure 6A:
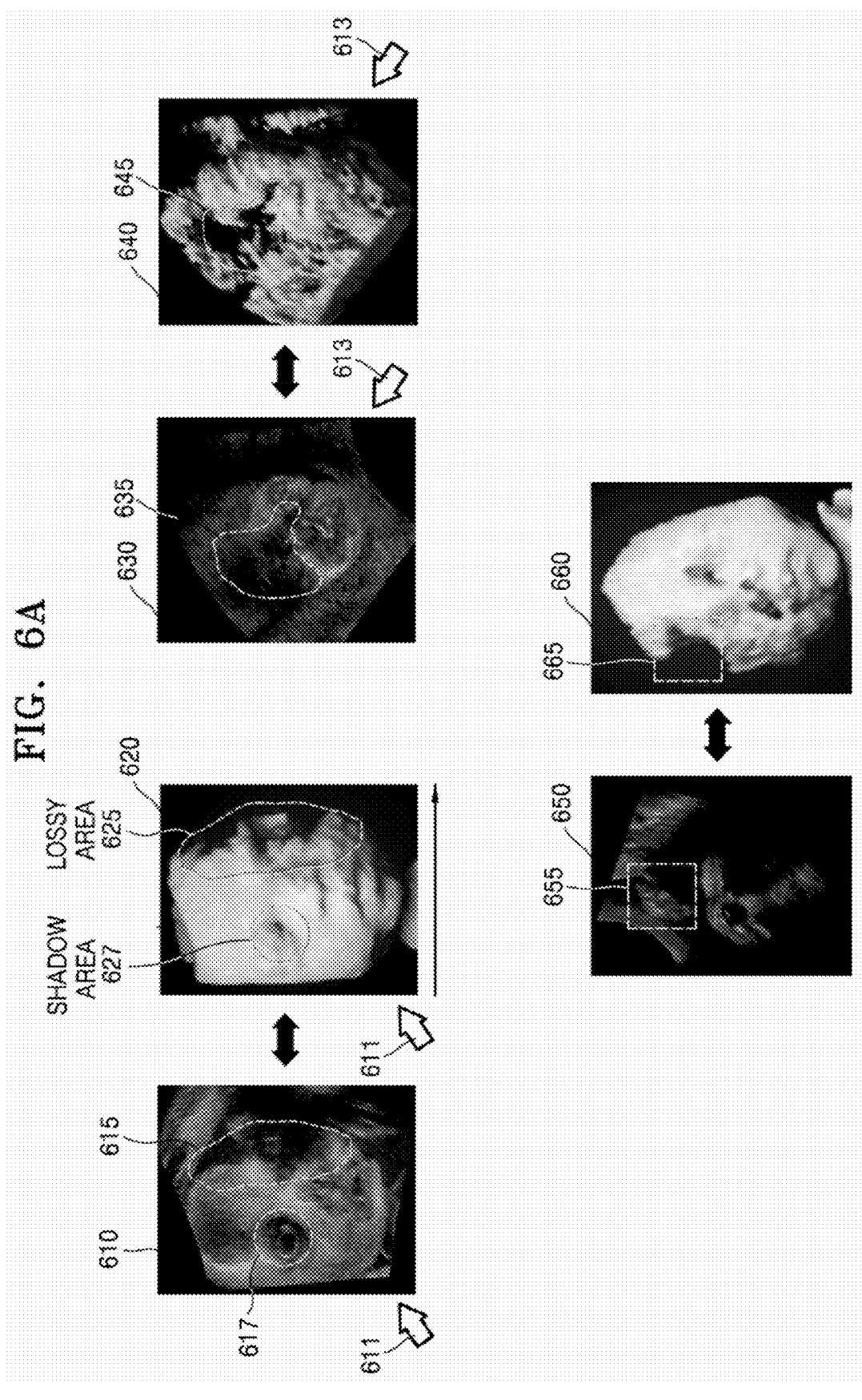
FIG. 6A illustrates a method by which an ultrasound imaging apparatus determines a lossy area, according to an embodiment.

FIG. 6A illustrates a method by which the ultrasound imaging apparatus 40 determines a lossy area, according to an embodiment.

Referring to FIG. 6A, the ultrasound imaging apparatus 40 may determine a lossy area 625 or 645 in a 2D rendered image 620 or 640 based on ultrasound volume data and a beam direction of the ultrasound signal.

When the ultrasound signal transmitted to the fetus meets a strong reflector (e.g., hand bones), the transmitted ultrasound signal may not pass through the strong reflector. Hence, the ultrasound signal hardly arrives at an area beyond the strong reflector in the transmitting direction of the ultrasound signal, so it may be difficult to receive an ultrasound echo signal from the area beyond the strong reflector. In this case, for the area to which the ultrasound signal fails to be delivered due to the strong reflector, the data value may appear to be equal to or less than a threshold value in the ultrasound volume data. The area to which the ultrasound signal fails to be delivered due to the strong reflector may be referred to as a lossy volume area. When the lossy volume area is rendered in a 2D image, the lossy volume area may appear to be a lossy area 625, 645 or 665 in which a portion of the face of the fetus is not represented as in right images 620, 640 and 660 of FIG. 6. Furthermore, due to the lossy volume area, cross-sectional images 610, 630 and 650 of the ultrasound volume data may also include lossy areas 615, 635 and 655.

In an embodiment, the ultrasound imaging apparatus 40 may determine the lossy area 615 in the ultrasound cross-sectional image 610, which is a piece of cross-sectional data that represents the face of the fetus in the ultrasound volume data, and determine the area 625 in the 2D rendered image 620 corresponding to the determined lossy area 615 as a lossy area in the 2D rendered image 620.

The ultrasound imaging apparatus 40 may select one of a plurality of cross-sections in the ultrasound volume data as the ultrasound cross-sectional image. For example, the ultrasound imaging apparatus 40 may select a cross-sectional image obtained by cutting a 3D volume formed by the ultrasound volume data in a coronal plane from among the plurality of cross-sections. Furthermore, for example, the ultrasound imaging apparatus 40 may select a cross-section with the biggest eye area of the fetus from among cross-sections parallel with the coronal plane of the ultrasound volume data.

The ultrasound imaging apparatus 40 may determine a head area of the fetus above the neck in the selected cross-section data 610. For example, the ultrasound imaging apparatus 40 may determine the head area of the fetus based on an outline of the head including the face and at least one of locations of eyes, nose and mouth. The head area of the fetus may include an area corresponding to the actual head of the fetus or the lossy area 615 having a data value less than a threshold value due to a strong reflector.

As the head area of the fetus is determined in the cross-section data 610, the ultrasound imaging apparatus 40 may identify an area having a data value equal to or less than the threshold value in the head area of the fetus. The area having the data value equal to or less than the threshold value in the head area of the fetus may include an eye area 617 of the fetus in addition to the lossy area 615.

The ultrasound imaging apparatus 40 may identify the lossy area 615 of the area having the data value equal to or less than the threshold value based on an irradiation direction 611 of the ultrasound signal. For example, the eye area 617 of the fetus may have an area which has the data value equal to or less than the threshold value and represents a round shape corresponding to an eyeball shape, regardless of the beam direction. On the other hand, in the lossy area 615, areas having data values equal to or less than the threshold value may appear continuously in the beam direction. Hence, the ultrasound imaging apparatus 40 may identify the area 615 in which the areas having data values equal to or less than the threshold value continue in the beam direction 611 as the lossy area in the head area of the fetus in the cross-sectional data 610.

In an embodiment, the ultrasound imaging apparatus 40 may determine a lossy volume area in the ultrasound volume data, and determine an area 625 of the 2D rendered image corresponding to the determined lossy volume area as a lossy area.

The ultrasound imaging apparatus 40 may determine a volume area corresponding to the head of the fetus among the ultrasound volume data before identifying the lossy area. For example, the ultrasound imaging apparatus 40 may determine the volume area corresponding to the head of the fetus based on the shape of the head and locations of eyes, nose and mouth. The volume area corresponding to the head of the fetus may include an area corresponding to an actual head of the fetus or the lossy volume area having a data value less than the threshold value due to a strong reflector.

As the volume area corresponding to the head of the fetus is determined, the ultrasound imaging apparatus 40 may identify a volume area having a data value equal to or less than the threshold value in the volume area corresponding to the head of the fetus. The volume area having the data value equal to or less than the threshold value in the volume area corresponding to the head of the fetus may include a volume area corresponding to an eye of the fetus in addition to the lossy volume area.

The ultrasound imaging apparatus 40 may identify the lossy volume area among the volume area having a voxel value equal to or less than a threshold value based on the irradiation direction 611 of the ultrasound signal. For example, the volume area corresponding to an eye of the fetus may have a volume area which has a voxel value equal to or less than the threshold value and represents a spherical shape corresponding to an eyeball shape, regardless of the beam direction. On the other hand, in the lossy volume area, areas having voxel values equal to or less than the threshold value may appear continuously in the beam direction. Hence, the ultrasound imaging apparatus 40 may determine an area in which there are continuous areas having voxel values equal to or less than the threshold value in the beam direction 611 as the lossy volume area among the volume area corresponding to the head of the fetus.

In an embodiment, as the lossy area 625 is determined, the ultrasound imaging apparatus 40 may restore the lossy area 625 even without an extra user input. In an embodiment, the ultrasound imaging apparatus 40 may indicate the lossy area 615 or 625 on the ultrasound cross-sectional image 610 or the 2D rendered image 620 of the face of the fetus, and restore the lossy area 615 or 625 when a user input to restore the indicated area is received.

Referring to the second images in FIG. 6A, likewise, the ultrasound imaging apparatus 40 may determine the lossy area 635 in the ultrasound volume data 630 based on the ultrasound volume data 630 and the beam direction 613, and determine the area 645 in the 2D rendered image corresponding to the determined lossy area 635 as a lossy area in the 2D rendered image 620.

Referring to lower images in FIG. 6A, likewise, the ultrasound imaging apparatus 40 may determine the lossy area 655 in the ultrasound volume data 650 based on the ultrasound volume data 650 and the beam direction. Furthermore, the ultrasound imaging apparatus 40 may determine the area 665 of the 2D rendered image corresponding to the determined lossy area 655 as a lossy area in the 2D rendered image 660.

In an embodiment, as the deeper the depth in the beam direction, the more the data loss occurs, the ultrasound imaging apparatus 40 may restore the lossy area by increasing restoration strength the deeper the depth in the beam direction.

Figure 6B:
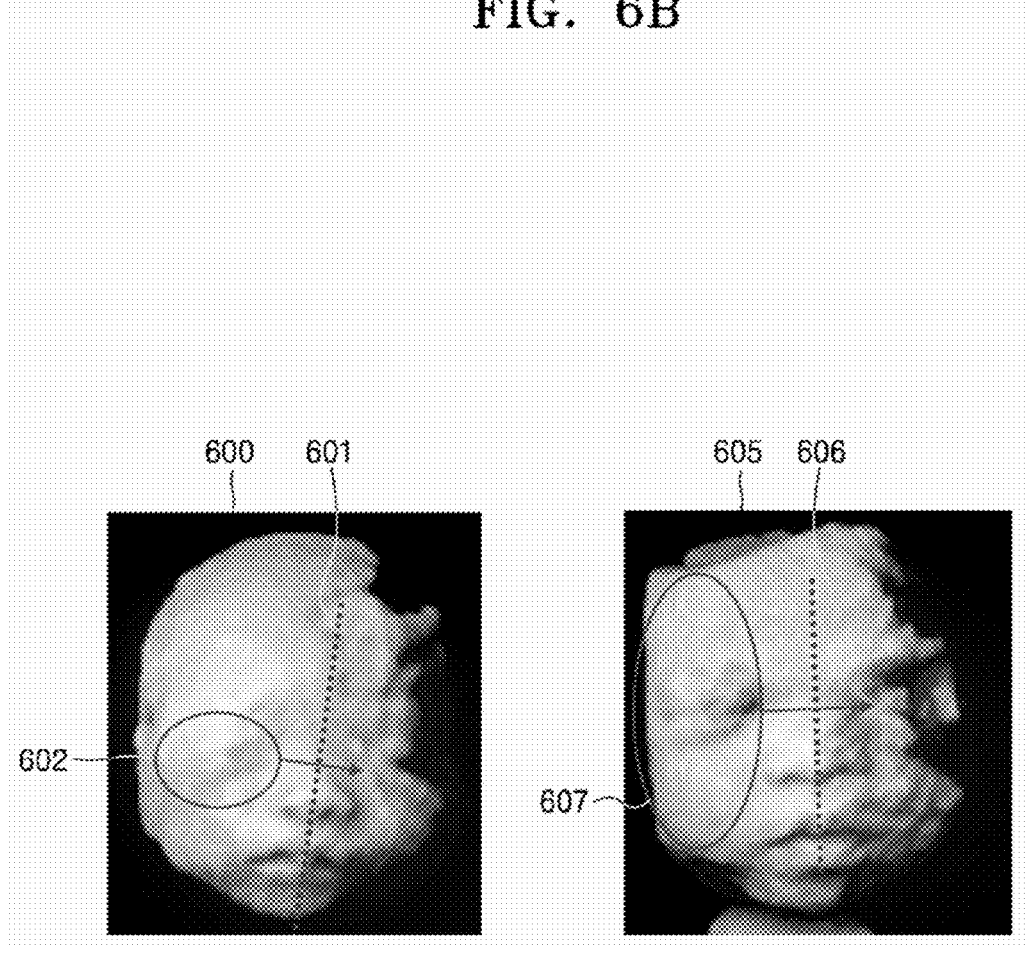
FIG. 6B illustrates a method by which an ultrasound imaging apparatus restores a lossy area, according to an embodiment.

FIG. 6B illustrates a method by which the ultrasound imaging apparatus 40 restores a lossy area, according to an embodiment.

Referring to FIG. 6B, the ultrasound imaging apparatus 40 may restore the lossy area by using symmetry of the face of the fetus.

In an embodiment, the ultrasound imaging apparatus 40 may restore the lossy area based on the symmetry of the face of the fetus in the 2D rendered image 600 or 605.

Referring to a left image 600 of FIG. 6B, the ultrasound imaging apparatus 40 may determine a base line 601 that connects the nose to the center of the mouth of the fetus on the 2D rendered image, and restore a right eye area that is lossy to be symmetrical to a left eye area 602 with respect to the base line 601.

Referring to a right image 605 of FIG. 6B, the ultrasound imaging apparatus 40 may determine a base line 606 that connects the nose to the mouth of the fetus on the 2D rendered image, and restore a right area that is lossy to be symmetrical to a left area 607 of the face.

In an embodiment, the ultrasound imaging apparatus 40 may restore the lossy area based on the symmetry of the face of the fetus in the ultrasound volume data. For example, the ultrasound imaging apparatus 40 may determine a data value of a portion that is symmetrical to the lossy volume area to be the data value of the lossy volume area based on the median plane of the ultrasound volume data. For example, when the volume area corresponding to the right eye of the fetus is lossy, the ultrasound imaging apparatus 40 may determine a data value of the volume area corresponding to the left eye of the fetus to be a data value of the volume area corresponding to the right eye. After the lossy volume area is filled with data, the ultrasound imaging apparatus 40 may display a 2D rendered image with the lossy area restored by rendering the ultrasound volume data.

Furthermore, after the lossy volume area is filled with data, the ultrasound imaging apparatus 40 may obtain a restored ultrasound cross-sectional image at a location of the ultrasound cross-sectional image 610 among the ultrasound volume data. For example, the ultrasound imaging apparatus 40 may obtain cross-section data at a location where data of the ultrasound cross-sectional image 610 is obtained among the ultrasound volume data as restored ultrasound cross-sectional image. The ultrasound imaging apparatus 40 may display the restored ultrasound cross-sectional image.

As a viewing point of the 3D volume data or beam direction needs to be taken into account to render the 3D volume data into a 2D rendered image, more natural 2D rendered image may be provided by restoring the lossy area with the use of the ultrasound volume data instead of restoring the lossy area in the 2D rendered image itself. Furthermore, even when a user input to change the viewpoint of the 3D volume data is received, without a need to generate a 2D rendered image based on the changed viewpoint and restore the lossy area based on the generated 2D rendered image, the ultrasound imaging apparatus 40 may provide a 2D rendered image with the lossy area restored by using the ultrasound volume data with the lossy volume area restored.

In an embodiment, the ultrasound imaging apparatus 40 may provide the 2D rendered image with the lossy area restored by using an AI model.

For example, the ultrasound imaging apparatus 40 may input the ultrasound volume data to an AI model and obtain the ultrasound volume data with the lossy volume area restored as an output of the AI model. For this, the ultrasound volume data including the lossy volume area may be selected as input data of training data of the AI model, and ultrasound volume data with the lossy volume area filled may be selected as output data of the training data of the AI model.

As the ultrasound volume data with the lossy volume area restored is obtained as an output of the AI model, the ultrasound imaging apparatus 40 may output a 2D rendered image with the lossy area restored by rendering the obtained ultrasound volume data.

In an embodiment, the ultrasound imaging apparatus 40 may restore a lossy volume area in first ultrasound volume data by using second ultrasound volume data having a different beam direction for the same fetus. For example, the ultrasound imaging apparatus 40 may identify an area of the second ultrasound volume data having the different beam direction, the area corresponding to the lossy volume area in the first ultrasound volume data, and determine a voxel value of the identified area to be a voxel value of the lossy volume area.

Figure 6C:
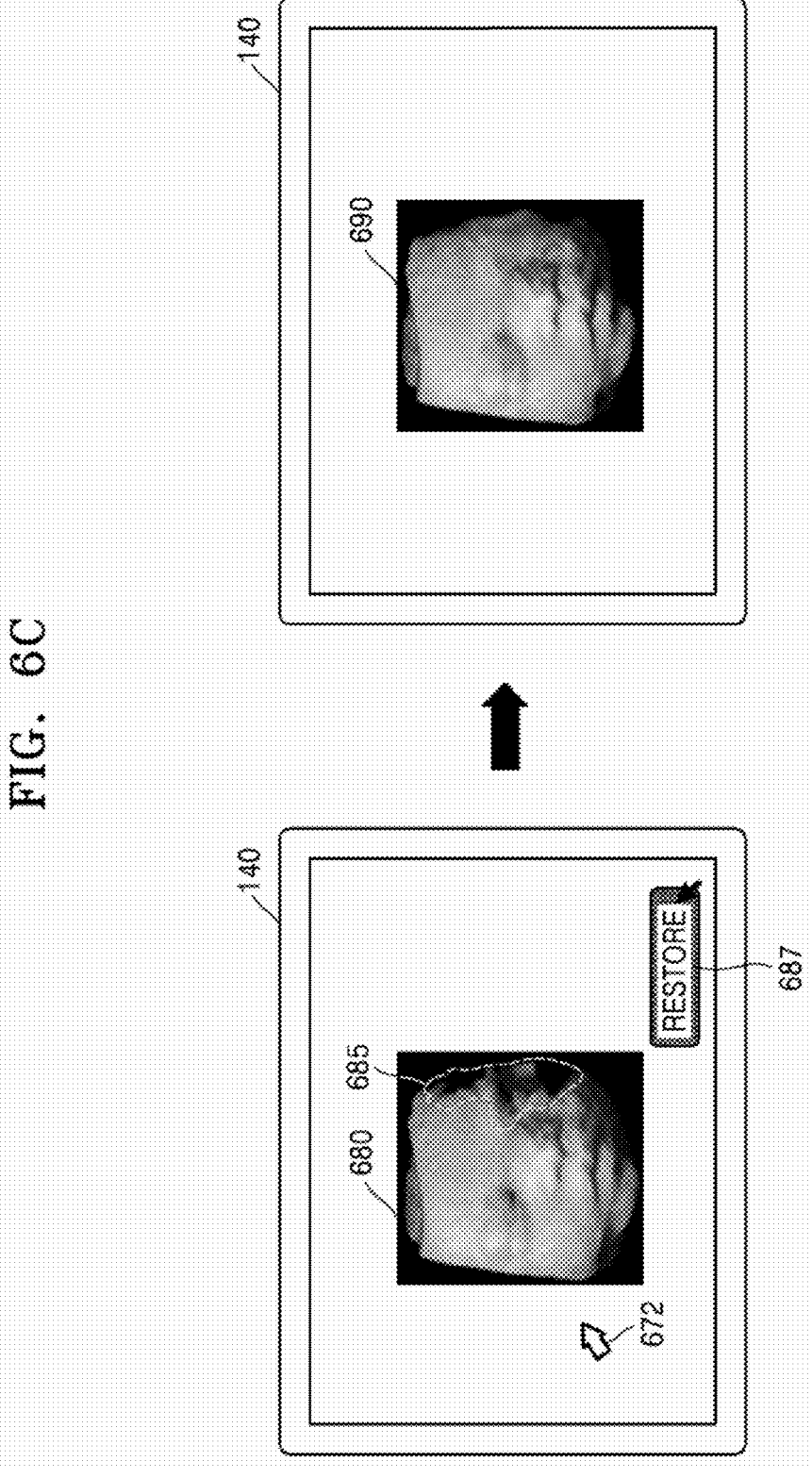
FIG. 6C illustrates a method by which an ultrasound imaging apparatus restores a lossy area based on a user input, according to an embodiment.

FIG. 6C illustrates a method by which the ultrasound imaging apparatus 40 restores a lossy area based on a user input, according to an embodiment.

Referring to a left image of FIG. 6C, on receiving a user input to modify the face of the fetus, the ultrasound imaging apparatus 40 may determine a lossy area 685 in a 2D rendered image 680, and display the 2D rendered image 680 with the lossy area 685 indicated therein. In an embodiment, the ultrasound imaging apparatus 40 may display an image that indicates a beam direction 672 along with the 2D rendered image 680 with the lossy area 685 indicated therein on the display 140.

Referring to a right image of FIG. 6C, on receiving a user input to restore the indicated lossy area 685, the ultrasound imaging apparatus 40 may restore the indicated lossy area 685 and display a restored 2D rendered image 690 on the display 140.

The user input to restore the indicated lossy area 685 may include, but not exclusively, a user input of manipulating a predetermined hardware button corresponding to a restoration function or a user input of selecting a displayed software button 687 corresponding to the restoration function.

In an embodiment, an interface for the left image of FIG. 6C may be displayed on the touch pad 122 (see FIGS. 2A and 2B) of the ultrasound imaging apparatus 40, and an interface for the right image of FIG. 6C may be displayed on the main screen 121 (see FIGS. 2A and 2B) of the ultrasound imaging apparatus 40.

In an embodiment, the ultrasound imaging apparatus 40 may indicate the lossy area 685 on the 2D rendered image 680, and display a phrase or an image indicating that it is a lossy area due to a strong reflector.

By indicating the lossy area on the 2D rendered image, the user may recognize a location of the lossy area and a location of a restorable area.

Figure 7:
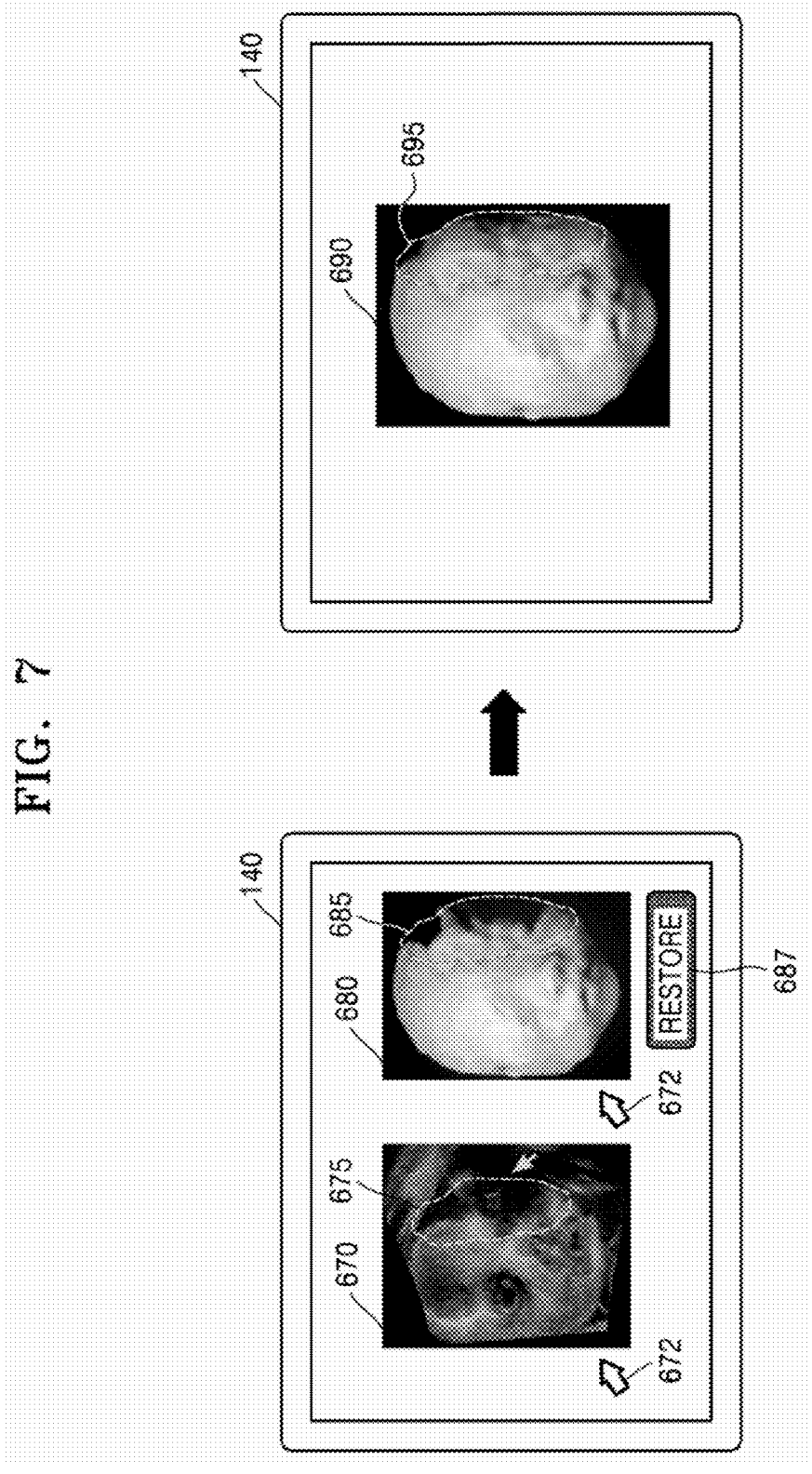
FIG. 7 illustrates a method by which an ultrasound imaging apparatus receives a user input to select an area to be restored from ultrasound volume data, according to an embodiment.

FIG. 7 illustrates a method by which the ultrasound imaging apparatus 40 receives a user input to select an area to be restored from ultrasound volume data, according to an embodiment.

Referring to FIG. 7, the ultrasound imaging apparatus 40 may receive a user input to select an area 675 to be restored on a cross-sectional image 670 of the ultrasound volume data, restore the 2D rendered image 680 based on the selected area 675 to be restored, and display a restored 2D rendered image 690.

Referring to a left image of FIG. 7, based on a user input to modify the face of the fetus in a 2D rendered image being received, the ultrasound imaging apparatus 40 may display the cross-sectional image 670 of the face of the fetus among the ultrasound volume data. Furthermore, in an embodiment, the ultrasound imaging apparatus 40 may display the image 672 indicating a beam direction for the cross-sectional image 670 along with the cross-sectional image 670.

In an embodiment, the ultrasound imaging apparatus 40 may receive a user input to select the area 675 to be restored on the cross-sectional image 670. For example, the ultrasound imaging apparatus 40 may display a closed curve on the cross-sectional image 670, and receive a user input to adjust the position of the closed curve.

In an embodiment, the ultrasound imaging apparatus 40 may determine a lossy area and recommend the determined lossy area as an area to be restored.

For example, the ultrasound imaging apparatus 40 may determine a lossy volume area based on the ultrasound volume data and the beam direction 672, determine a lossy area in the cross-sectional image 670 based on the lossy volume area, and display the closed curve 675 that indicates the determined lossy area on the cross-sectional image 670. Furthermore, the ultrasound imaging apparatus 40 may display the closed curve 685 that indicates an area corresponding to the lossy area in the cross-sectional image 670 on the 2D rendered image 680.

Moreover, the ultrasound imaging apparatus 40 may receive a user input to select an area to be restored by adjusting the recommended lossy area. For example, the ultrasound imaging apparatus 40 may receive a user input to adjust the position of the closed curve on the cross-sectional image 670. On receiving the user input to adjust the position of the closed curve 675 on the cross-sectional image 670, the ultrasound imaging apparatus 40 may adjust the position of the closed curve 685 on the 2D rendered image 680 so that the area of the closed curve 685 on the 2D rendered image 680 corresponds to the area of the closed curve 675 in the cross-sectional image 670.

A strong reflector may be easily identified in the cross-sectional image 670 rather than in the 2D rendered image and may be displayed along with the beam direction so that the user may more accurately select the location of the strong reflector and the lossy area in the cross-sectional image 670. Furthermore, the ultrasound imaging apparatus 40 may determine the area of the closed curve 685 on the 2D rendered image 680 as an area to be restored.

In an embodiment, on receiving the user input to adjust the position of the closed curve 685 on the 2D rendered image 680, the ultrasound imaging apparatus 40 may adjust the position of the closed curve 675 in the cross-sectional image 670 so that the area of the closed curve 675 in the cross-sectional image 670 corresponds to the area of the closed curve 685 in the 2D rendered image 680.

On receiving a user input to restore the area to be restored (the area of the closed curve 685), the ultrasound imaging apparatus 40 may restore the area to be restored and display the restored 2D rendered image 690 on the display 140, as shown in a right image of FIG. 7.

In an embodiment, on receiving a user input to restore the area to be restored, the ultrasound imaging apparatus 40 may display the cross-sectional image 670 with the area 675 to be restored therein.

In an embodiment, an interface for the left image of FIG. 7 may be displayed on the touch pad 122 (see FIGS. 2A and 2B) of the ultrasound imaging apparatus 40, and an interface for the right image of FIG. 7 may be displayed on the main screen 121 (see FIGS. 2A and 2B) of the ultrasound imaging apparatus 40.

Figure 8:
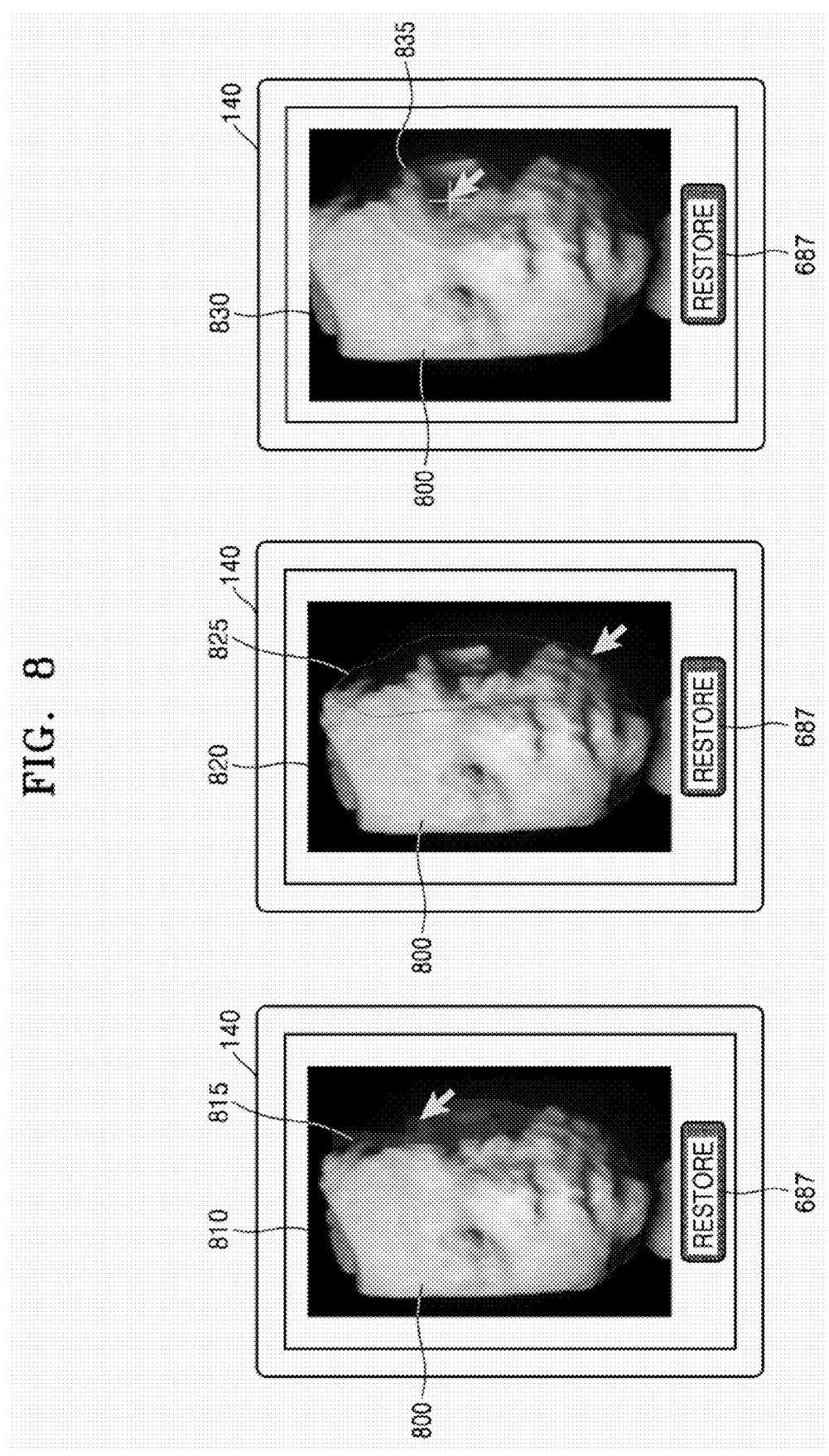
FIG. 8 illustrates a method by which an ultrasound imaging apparatus receives a user input to select an area to be restored on a 2D rendered image, according to an embodiment.

FIG. 8 illustrates a method by which the ultrasound imaging apparatus 40 receives a user input to select an area to be restored on a 2D rendered image, according to an embodiment.

Referring to FIG. 8, on receiving a user input to modify the face of the fetus, the ultrasound imaging apparatus 40 may display a 2D rendered image 810, 820 or 830 on the display 140. The ultrasound imaging apparatus 40 may receive a user input to select an area to be restored on the 2D rendered image through an input interface such as a touch pad, a mouse, a keyboard or a trackball.

Referring to a first image of FIG. 8, the ultrasound imaging apparatus 40 may receive a user input to select an area 815 to be restored on the 2D rendered image 810 through a user interface that represents a brush effect. The user interface that represents the brush effect may be a user interface that shows such an effect as if an area on which a cursor passes is painted with a brush. In this case, the brush effect may be represented in a predetermined color and displayed translucently such that a face 800 of the fetus is visible in the 2D rendered image 810.

Referring to a second image of FIG. 8, the ultrasound imaging apparatus 40 may receive a user input to select an area 825 to be restored on the 2D rendered image 820 through a user interface for designating an edge of an area to be restored. In this case, the position of the edge of the area to be restored 825 may be changed by cursor movement.

Referring to a third image of FIG. 8, on receiving a user input to select an arbitrary location on the 2D rendered image 820, the ultrasound imaging apparatus 40 may select an area of a predetermined shape centered on the selected location as an area 835 to be restored.

Furthermore, based on a user input to restore the selected area to be restored 815, 825 or 835 being received, the ultrasound imaging apparatus 40 may restore the selected area to be restored 815, 825 or 835 and display a 2D rendered image with the selected area to be restored 815, 825 or 835 restored therein.

The user input to restore the selected area to be restored 815, 825 or 835 may include a user input of selecting a 'restore' button 687 displayed on the display 140.

In an embodiment, the ultrasound imaging apparatus 40 may limit the size of the area to be restored to a predetermined percentage (e.g., 15%) or less of the full image so that the user is unable to overly widen the area to be restored. The ultrasound imaging apparatus 40 basically outputs ultrasound images for diagnosis, so it may limit the size of the area to be restored to prevent the user from excessively widening the area to be restored.

Figure 9:
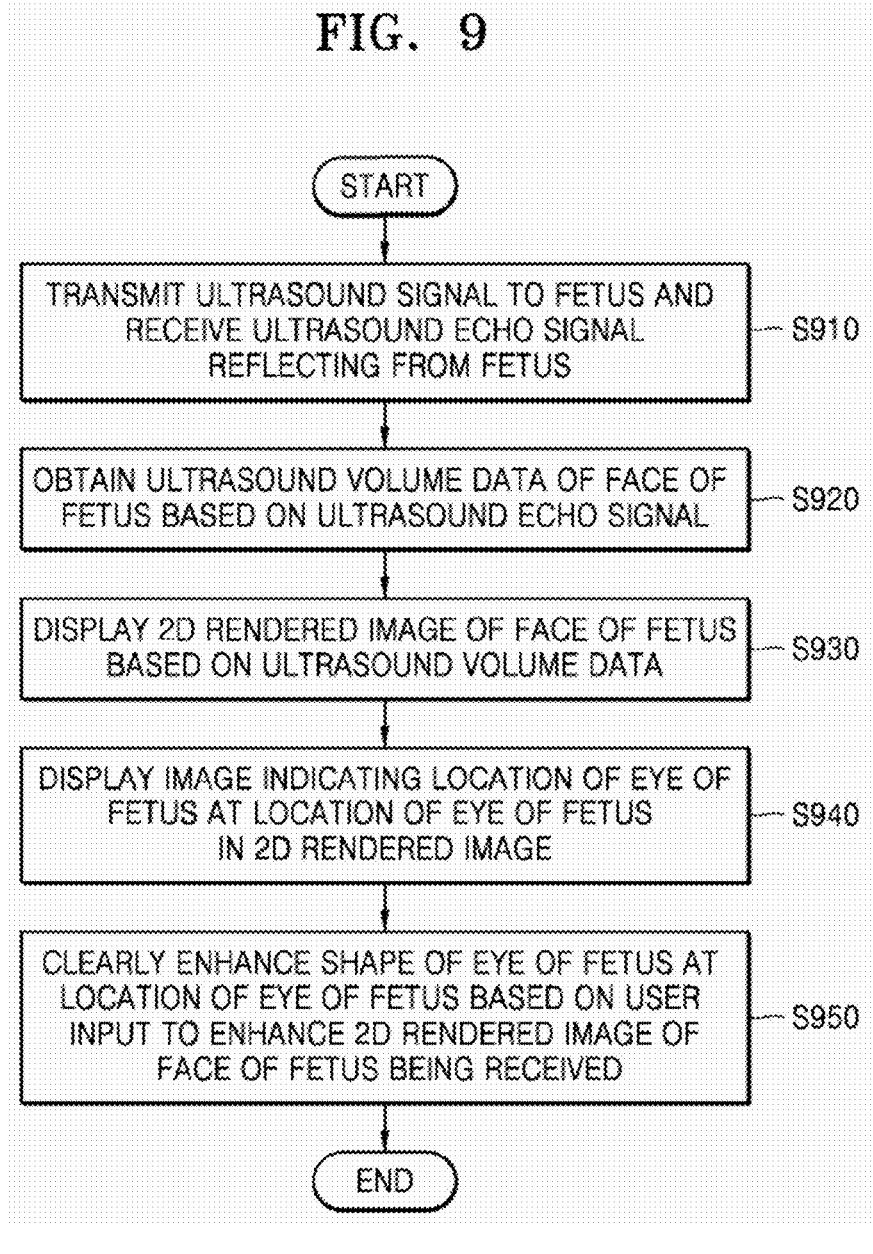
FIG. 9 is a flowchart of a method by which an ultrasound imaging apparatus clearly enhances a face of a fetus, according to an embodiment.

FIG. 9 is a flowchart of a method by which the ultrasound imaging apparatus 40 clearly enhances a face of a fetus, according to an embodiment.

In operation S910, the ultrasound imaging apparatus 40 may transmit an ultrasound signal to a fetus and receive an ultrasound echo signal reflecting from the fetus. In operation S920, the ultrasound imaging apparatus 40 may obtain ultrasound volume data of the face of the fetus based on the ultrasound echo signal.

Operations S910 and S920 may be described with reference to operation S510 and S520 of FIG. 5.

In operation S930, the ultrasound imaging apparatus 40 may display a 2D rendered image of the face of the fetus based on ultrasound volume data.

The 2D rendered image of the face of the fetus obtained from the ultrasound volume data may or may not include a lossy area not represented of the face of the fetus.

In a case that the 2D rendered image includes no lossy area, the ultrasound imaging apparatus 40 may not restore the lossy area. Also in a case that a lossy area is included but no user input to restore the lossy area is received, the ultrasound imaging apparatus 40 may not restore the lossy area.

In operation S940, the ultrasound imaging apparatus 40 may display an image indicating a location of an eye of the fetus at the location of the eye of the fetus in the 2D rendered image.

The ultrasound imaging apparatus 40 may determine a location of a landmark (e.g., eye, nose or mouth) of the face in the 2D rendered image.

The ultrasound imaging apparatus 40 may also display an image indicating a location of the landmark at the location of the landmark determined in the 2D rendered image.

In operation S950, the ultrasound imaging apparatus 40 may clearly enhance the shape of an eye of the fetus at the location of the eye of the fetus, based on a user input to enhance the 2D rendered image of the face of the fetus being received.

Figure 10:
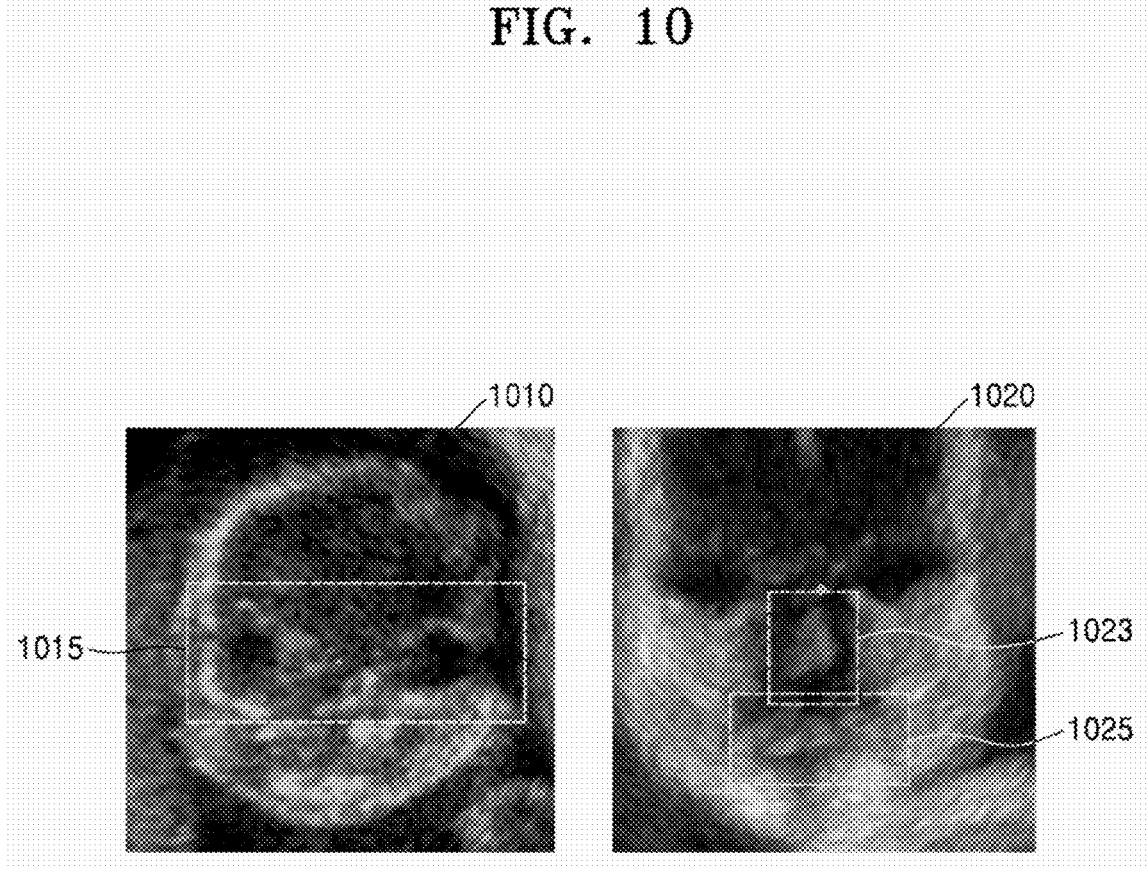
FIG. 10 illustrates a method by which an ultrasound imaging apparatus determines a location of a landmark of a face based on ultrasound volume data, according to an embodiment.

FIG. 10 illustrates a method by which the ultrasound imaging apparatus 40 determines a location of a landmark of a face based on ultrasound volume data, according to an embodiment.

Referring to FIG. 10, the ultrasound imaging apparatus 40 may determine a location of a landmark of the face based on ultrasound volume data, and display the determined location of the landmark on a cross-sectional image 1010 or 1020 of the ultrasound volume data. Furthermore, the ultrasound imaging apparatus 40 may determine a location on the 2D rendered image corresponding to the determined location of the landmark as a location of the landmark in the 2D rendered image. The ultrasound imaging apparatus 40 may also indicate the determined location of the landmark on the 2D rendered image.

The landmark of the face may include an eye, a nose or a mouth, without being limited thereto. The ultrasound imaging apparatus 40 may determine a location of the landmark of the face in the ultrasound volume data based on the outline of the face, a predetermined shape of the landmark and characteristics of an ultrasound echo signal received from the landmark.

When the fetus's eyes are closed or due to the influence of the amniotic fluid, the eyes of the fetus tend to appear to be unclear in the 2D rendered image. Hence, the eyes of the fetus need to be clearly enhanced, and in this case, it is important to correctly find the location of the eyes of the fetus in the 2D rendered image. It is relatively easy to find the location of the nose or mouth of the fetus because the nose or mouth of the fetus is represented as protruding in the 2D rendered image, while it is difficult to find the location of the eyes in the 2D rendered image because the eyes are frequently represented as sleeky which are difficult to distinguish from surrounding areas in the 2D rendered image.

On the other hand, characteristics of the landmark is relatively clear in the ultrasound volume data. Hence, the ultrasound imaging apparatus 40 may determine a location of the landmark in the ultrasound volume data, and determine a location in the 2D rendered image corresponding to the determined location of the landmark as a location of the landmark in the 2D rendered image. The ultrasound imaging apparatus 40 may also indicate the determined location of the eye on the 2D rendered image.

For example, an eye bone within which an eye ball is located in the ultrasound volume data or cross-sectional image has a data value equal to or greater than a threshold, while the eye ball within the eye bone may have a data value less than the threshold like a fluid. As there is a big difference between the data value corresponding to the eye bone and the data value corresponding to the eye ball, an eye area in the ultrasound volume data or the cross-sectional image may have a high contrast ratio. Hence, when an area having a data value less than the threshold in the ultrasound volume data has a spherical shape and two volume areas each having the spherical shape are adjacent to each other, the ultrasound imaging apparatus 40 may identify the two volume areas as volume areas corresponding to the eyes.

Furthermore, for example, a nose bone in the ultrasound volume data may appear to be shaped like a triangular pyramid. Hence, the ultrasound imaging apparatus 40 may determine a volume area that represents a triangular pyramid shape under the eyes as an area corresponding to the nose.

Moreover, for example, the mouth may appear to be shaped like an oval sphere in the ultrasound volume data. Hence, the ultrasound imaging apparatus 40 may determine a volume area that represents the shape of an oval sphere under the nose as an area corresponding to the mouth.

As the volume areas corresponding to the landmarks in the ultrasound volume data are identified, the ultrasound imaging apparatus 40 may display the identified volume areas on one cross-sectional image in the ultrasound volume data.

For example, the ultrasound imaging apparatus 40 may select a cross-section having the highest contrast ratio of the eye outline among the cross-sections parallel to the coronal plane, and display an image 1015 indicating a location of eyes at the location of the eyes in the selected cross-sectional image 1010.

Furthermore, for example, the ultrasound imaging apparatus 40 may select a cross-section having the highest contrast ratio of the nose outline among the cross-sections parallel to the coronal plane, and display images 1023 and 1025 indicating locations of nose and mouth at the locations of the nose and mouth in the selected cross-sectional image 1020.

Figure 11:
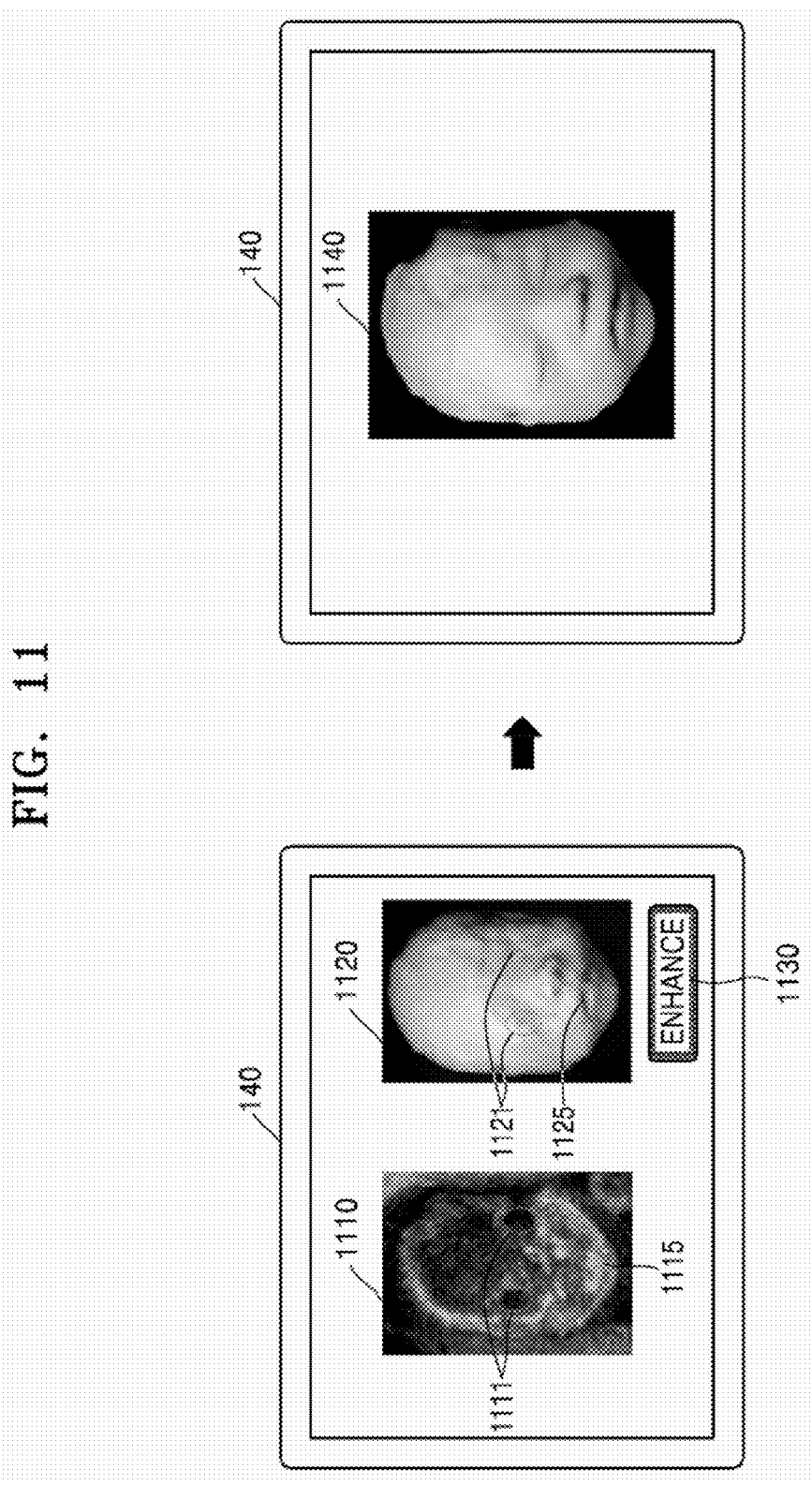
FIG. 11 illustrates a method by which an ultrasound imaging apparatus indicates a location of a landmark on a 2D rendered image, according to an embodiment.

FIG. 11 illustrates a method by which the ultrasound imaging apparatus 40 indicates locations of landmarks on a 2D rendered image, according to an embodiment.

Referring to FIG. 11, the ultrasound imaging apparatus 40 may indicate locations 1121 and 1125 of landmarks on a 2D rendered image 1120. Furthermore, on receiving a user input to enhance the 2D rendered image 1120, the ultrasound imaging apparatus 40 may clearly enhance the landmarks based on the locations 1121 and 1125 of the landmarks indicated on the 2D rendered image 1120. The ultrasound imaging apparatus 40 may display an enhanced 2D rendered image 1140 on the display 140.

In an embodiment, the ultrasound imaging apparatus 40 may determine locations of the landmarks based on the ultrasound volume data, and display images 1111 and 1115 indicating the determined locations of the landmarks on a cross-sectional image 1110. For example, the ultrasound imaging apparatus 40 may display the image 1111 indicating the locations of eyes and the image 1115 indicating the mouth on the cross-sectional image 1110.

The ultrasound imaging apparatus 40 may also display an image 1121 indicating locations of eyes at locations on the 2D rendered image corresponding to the locations of the eyes on the cross-sectional image 1110. The ultrasound imaging apparatus 40 may also display an image 1125 indicating a location of the mouth at a location on the 2D rendered image corresponding to the location of the mouth on the cross-sectional image 1110.

In an embodiment, the ultrasound imaging apparatus 40 may display an image representing a shape of the landmark at the location of the landmark. For example, the ultrasound imaging apparatus 40 may display an eye shaped image at the locations of the eyes on the 2D rendered image 1120.

By displaying corresponding locations of the landmarks on the cross-sectional image 1110 and the 2D rendered image 1120, the use may identify that the locations of the landmarks displayed on the 2D rendered image 1120 is determined based on the ultrasound volume data. The user may also identify whether the location of the landmark corresponds to a location of an actual landmark of the fetus based on the location of the landmark displayed on the cross-sectional image 1110.

The ultrasound imaging apparatus 40 may receive a user input to enhance the 2D rendered image. The user input to enhance the 2D rendered image may include, but not exclusively, a user input of manipulating a predetermined hardware button corresponding to an enhancement function or a user input of selecting a displayed software button 1130 corresponding to the enhancement function.

On receiving the user input to enhance the 2D rendered image 1120, the ultrasound imaging apparatus 40 may clearly enhance the face of the fetus based on the locations 1121 and 1125 of the landmarks on the 2D rendered image 1120. For example, the ultrasound imaging apparatus 40 may clearly enhance the eyes of the fetus at the locations 1121 of the eyes on the 2D rendered image 1120.

In an embodiment, the ultrasound imaging apparatus 40 may enhance the 2D rendered image by using an AI model. For example, the ultrasound imaging apparatus 40 may obtain a 2D rendered image 1140 with the landmark clearly enhanced at the location of the landmark from an output of the AI model that receives the 2D rendered image 1120 and the location of the landmark as inputs. For this, the AI model may be trained with the 2D rendered image and the location of the landmark as input data of training data and the 2D rendered image with the landmark clearly enhanced at the location of the landmark as output data of the training data.

Figure 12:
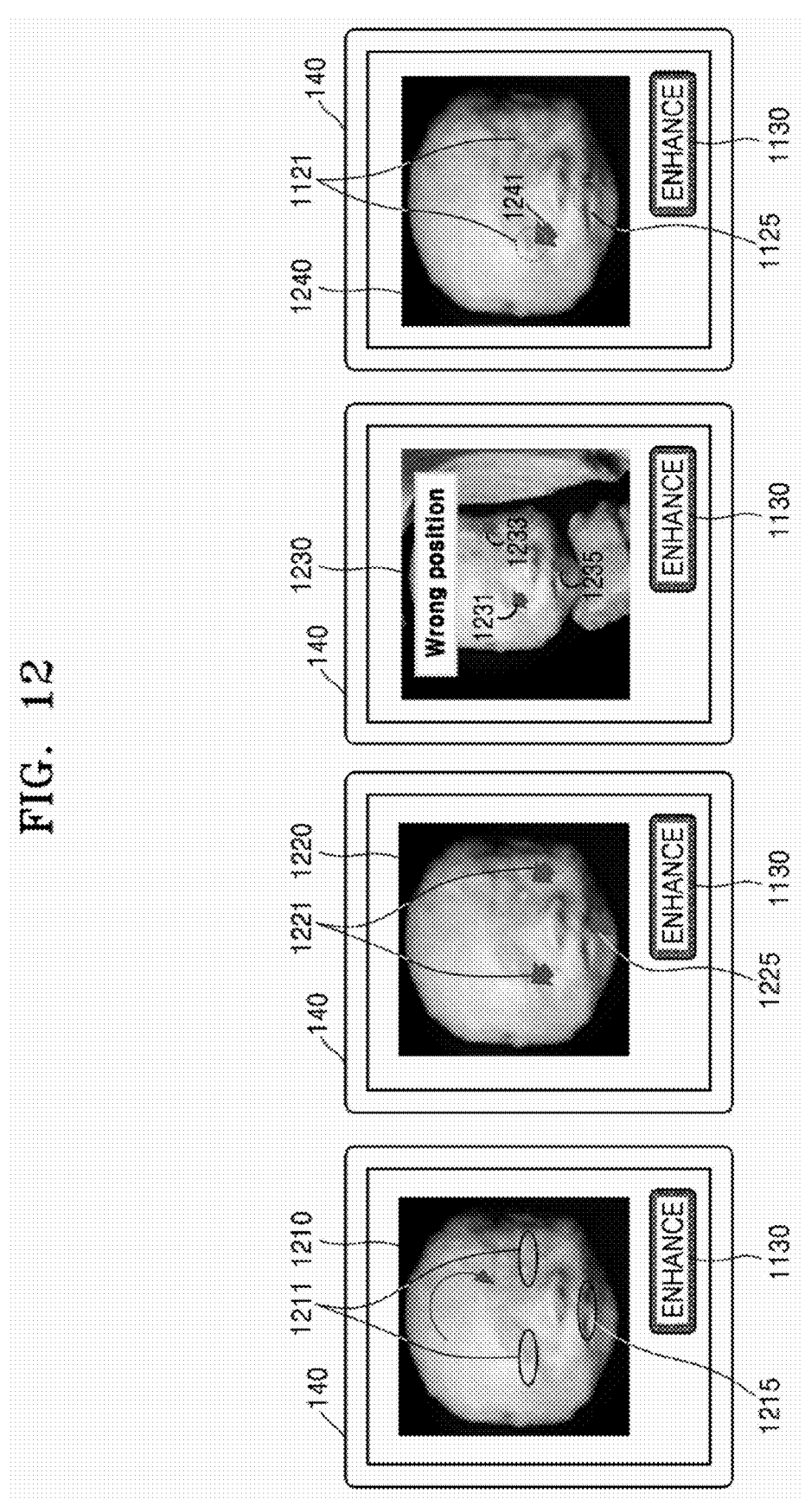
FIG. 12 illustrates a method by which an ultrasound imaging apparatus receives a user input to select a location of a landmark of a face on a 2D rendered image, according to an embodiment.

FIG. 12 illustrates a method by which the ultrasound imaging apparatus 40 receives a user input to select a location of a landmark of a face on a 2D rendered image, according to an embodiment.

Referring to FIG. 12, the ultrasound imaging apparatus 40 may display the 2D rendered image and receive a user input to select a location of a landmark on the 2D rendered image. The ultrasound imaging apparatus 40 may also enhance the 2D rendered image to make the landmark clear based on the selected location of the landmark.

Referring to a first image of FIG. 12, the ultrasound imaging apparatus 40 may display an image 1211 indicating the locations of the eyes of the fetus and an image 1215 indicating the location of the mouth of the fetus on the 2D rendered image 1210. Positions of the images 1211 and 1215 may be fixed in the 2D rendered image 1210 without being changed. While the positions of the images 1211 and 1215 are fixed, the ultrasound imaging apparatus 40 may receive a user input to select a location of a landmark by receiving a user input to turn the head of the fetus such that the images 1211 and 1215 lie on the locations of the landmarks desired by the user or a user input to adjust the size of the head of the fetus. The user input to turn the head of the fetus may be referred to as geometry adjustment, and the user input to adjust the size of the fetus may be referred to as zoom control.

Referring to a second image of FIG. 12, the ultrasound imaging apparatus 40 may receive a user input to select a location of a landmark on the 2D rendered image with the cursor. The ultrasound imaging apparatus 40 may display the images 1221 and 1225 that indicate the location of the landmark selected by the user.

Referring to third image of FIG. 12, the ultrasound imaging apparatus 40 may determine whether the location of the landmark selected by the user is proper, and based on determining that it is not proper, output a notification indicating that the selected location of the landmark is not proper.

The ultrasound imaging apparatus 40 may determine a location of a landmark of the face in a 2D rendered image 1230 based on the ultrasound volume data. Furthermore, based on the location of the landmark selected by the user being out of a predetermined range from the determined location of the landmark, the ultrasound imaging apparatus 40 may output a notification indicating that the selected location of the landmark is not proper. For example, based on the selected location of the landmark determined to be improper, the ultrasound imaging apparatus 40 may display an image 1233 indicating the location of the landmark determined to be improper in a color different from images 1231 and 1235 indicating locations of landmarks determined to be proper. Furthermore, when receiving a user input to select a location of a landmark and the selected location of the landmark is determined to be improper, the ultrasound imaging apparatus 40 may display a phrase notifying that the selected location of the landmark is not proper.

Referring to a fourth image of FIG. 12, the ultrasound imaging apparatus 40 may determine locations of landmarks of the face in a 2D rendered image 1240 based on the ultrasound volume data, and display reference images 1121 and 1125 at the determined locations. The ultrasound imaging apparatus 40 may receive a user input to select a location of a landmark on the 2D rendered image with the reference images displayed thereon. The ultrasound imaging apparatus 40 may also display an image 1241 indicating the location selected by the user at the location of the landmark selected by the user along with the reference images.

On receiving the user input to enhance the 2D rendered image 1210, 1220, 1230 or 1240, the ultrasound imaging apparatus 40 may clearly enhance the face of the fetus by enhancing the landmark more clearly at the selected location of the landmark on the 2D rendered image 1210, 1220, 1230 or 1240.

Figure 13:
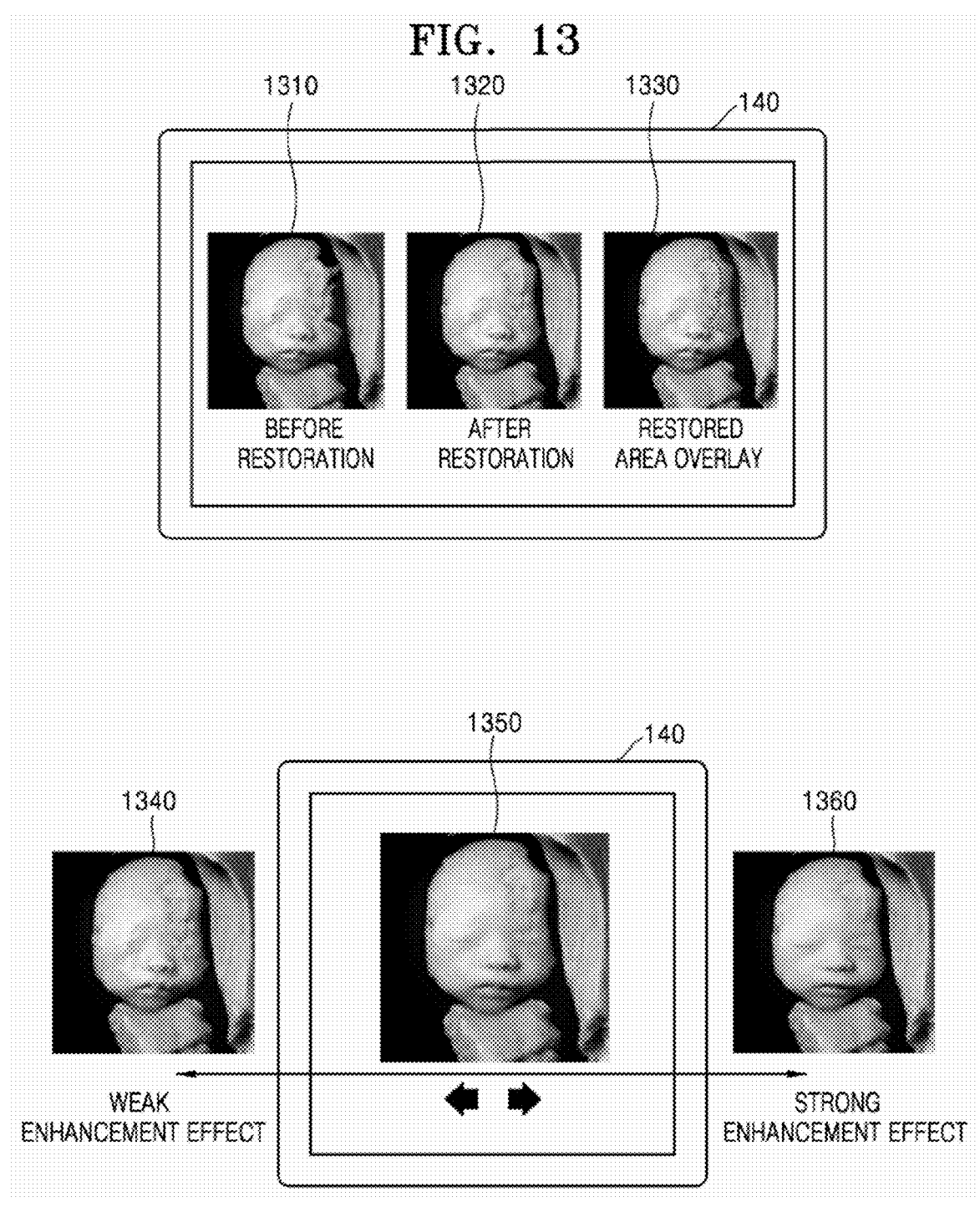
FIG. 13 illustrates a method by which an ultrasound imaging apparatus displays a 2D rendered image, according to an embodiment.

FIG. 13 illustrates a method by which the ultrasound imaging apparatus 40 displays a 2D rendered image, according to an embodiment.

Referring to an upper image of FIG. 13, the ultrasound imaging apparatus 40 may display both the 2D rendered image with the lossy area restored and the 2D rendered image before restoration.

The ultrasound imaging apparatus 40 may display a 2D rendered image 1310 before restoration, a 2D rendered image 1320 with a lossy area restored, and a 2D rendered image 1330 indicating a restored area all together.

Referring to a lower image of FIG. 13, on receiving a user input to select an enhancement level, the ultrasound imaging apparatus 40 may display an enhanced 2D rendered image corresponding to the selected enhancement level.

The ultrasound imaging apparatus 40 may clearly enhance a landmark of the face, and further enhance the face skin of the fetus more smoothly. Furthermore, when a higher enhancement level is selected, the ultrasound imaging apparatus 40 may increase the clarity of the landmark and enhance the face skin more smoothly.

The ultrasound imaging apparatus 40 may receive a user input to select an enhancement level. For example, the ultrasound imaging apparatus 40 may receive a user input to rotate a knob, determine an enhancement level corresponding to a degree of rotation, and display an enhanced 2D rendered image corresponding to the determined enhancement level. Furthermore, the ultrasound imaging apparatus 40 may determine a step size of the enhancement level to be changed in response to the rotation speed of the knob. Accordingly, as the rotation speed of the knob increases, images having a big difference in enhancement level may be sequentially displayed.

The ultrasound imaging apparatus 40 may display a restored 2D rendered image 1340 from the ultrasound volume data based on a user input to select a low enhancement level being received. Furthermore, the ultrasound imaging apparatus 40 may sequentially display enhanced 2D rendered images 1350 and 1360 based on a user input to increase the enhancement level being received.

Figure 14:
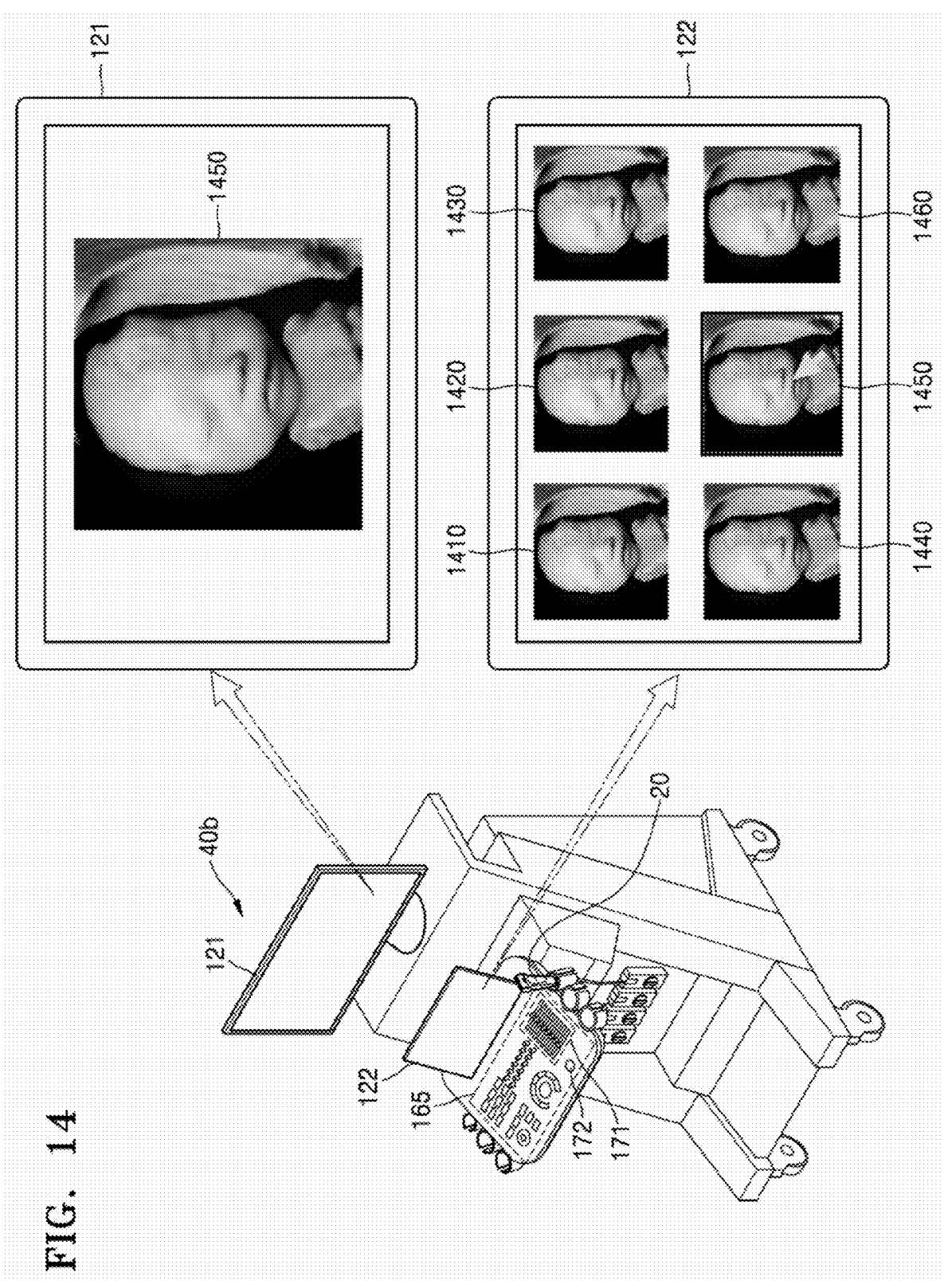
FIG. 14 illustrates a method by which an ultrasound imaging apparatus displays an enhanced 2D rendered image, according to an embodiment.

FIG. 14 illustrates a method by which the ultrasound imaging apparatus 40 displays an enhanced 2D rendered image, according to an embodiment.

Referring to FIG. 14, the ultrasound imaging apparatus 40 may display a plurality of 2D rendered images 1410 to 1460 on the sub-display 122, and display the 2D rendered image 1450 on the main display 121, which is selected by the user from among the plurality of 2D rendered images 1410 to 1460 displayed on the sub-display 122.

Accordingly, the user may show a 2D rendered image to a subject or a mother, the 2D rendered image being selected by the user from among a plurality of 2D rendered images having different enhancement levels or restoration degrees.

The machine-readable storage medium may be provided in the form of a non-transitory storage medium. The term 'non-transitory storage medium' may mean a tangible device without including a signal, e.g., electromagnetic waves, and may not distinguish between storing data in the storage medium semi-permanently and temporarily. For example, the non-transitory storage medium may include a buffer that temporarily stores data.

In an embodiment of the disclosure, the aforementioned method according to the various embodiments of the disclosure may be provided in a computer program product. The computer program product may be a commercial product that may be traded between a seller and a buyer. The computer program product may be distributed in the form of a machine-readable storage medium (e.g., a CD-ROM) or distributed directly between two user devices (e.g., smart phones) or online (e.g., downloaded or uploaded). In the case of the online distribution, at least part of the computer program product (e.g., a downloadable app) may be at least temporarily stored or arbitrarily created in a storage medium that may be readable to a device such as a server of the manufacturer, a server of the application store, or a relay server.

What is claimed is:

1. An ultrasound imaging apparatus comprising:
an ultrasound transceiver module;
a display;
an input interface; and
at least one processor,
wherein the at least one processor is configured to control the ultrasound transceiver module to transmit an ultrasound signal to a fetus and receive an ultrasound echo signal reflecting from the fetus,
obtain ultrasound volume data of a face of the fetus based on the ultrasound echo signal, the ultrasound volume data including a lossy volume area where the ultrasound echo signal has a value equal to or less than a threshold value due to a strong reflector,
display a two dimensional (2D) rendered image of the face of the fetus and an ultrasound cross-sectional image of the face of the fetus, based on the ultrasound volume data, through the display, the 2D rendered image and the ultrasound cross-sectional image including a lossy area not represented of the face of the fetus due to the lossy volume area,
indicate, on the 2D rendered image, an area for restoration including the lossy area,
indicate, on the cross-sectional image, an area corresponding to the area for restoration indicated in the 2D rendered image, and
restore the indicated area for restoration indicated on the 2D rendered image based on a user input received through the input interface.

2. The ultrasound imaging apparatus of claim 1, wherein the at least one processor is further configured to
determine the lossy volume area based on the ultrasound volume data and a direction in which the ultrasound signal is irradiated to the fetus,
determine the lossy area in the 2D rendered image and the ultrasound cross-sectional image based on the lossy volume area, indicate the determined lossy area in the 2D rendered image and the ultrasound cross-sectional image as the area for restoration, and display a direction image representing the direction in which the ultrasound signal is irradiated to the fetus.

3. The ultrasound imaging apparatus of claim 1, wherein the at least one processor is further configured to receive a user input to select an area for restoration on the displayed ultrasound cross-sectional image, and indicate an area selected on the ultrasound cross-sectional image and an area in the 2D rendered image corresponding to the selected area as the area for restoration.

4. The ultrasound imaging apparatus of claim 1, wherein the at least one processor is further configured to receive a user input to select the area for restoration on the 2D rendered image of the face of the fetus, and indicate the selected area for restoration on the 2D rendered image.

5. The ultrasound imaging apparatus of claim 1, wherein the at least one processor is further configured to display an image indicating a location of an eye of the fetus at the location of the eye of the fetus in the 2D rendered image, and clearly enhance a shape of the eye of the fetus at the location of the eye of the fetus based on a user input to enhance the 2D rendered image of the face of the fetus being received.

6. The ultrasound imaging apparatus of claim 5, wherein the at least one processor is further configured to determine a location of an eye of the fetus in the ultrasound volume data based on predetermined characteristics of the eye which appears in the ultrasound volume data, and determine a location on the 2D rendered image corresponding to the determined location of the eye of the fetus as a location of the eye of the fetus in the 2D rendered image.

7. The ultrasound imaging apparatus of claim 5, wherein the at least one processor is further configured to receive a user input to select an area of an eye of the fetus on the ultrasound cross-sectional image, and determine a location in the 2D rendered image corresponding to the selected area of the eye as a location of the eye of the fetus in the 2D rendered image.

8. The ultrasound imaging apparatus of claim 5, wherein the at least one processor is further configured to receive a user input to select a location of an eye of the fetus on the 2D rendered image of the face of the fetus.

9. The ultrasound imaging apparatus of claim 1, wherein the at least one processor is further configured to display both the 2D rendered image including the lossy area and the restored 2D rendered image.

10. The ultrasound imaging apparatus of claim 5, wherein the display comprises a main display and a sub-display, wherein the at least one processor is further configured to display a plurality of 2D rendered images on the sub-display, which have different enhancement levels and include the enhanced 2D rendered image, and based on a user input to select one of the plurality of 2D rendered images being received, display the selected 2D rendered image on the main display.

11. A method of controlling an ultrasound imaging apparatus, the method comprising:

transmitting an ultrasound signal to a fetus and receiving an ultrasound echo signal reflecting from the fetus;

obtaining ultrasound volume data of a face of the fetus based on the ultrasound echo signal, the ultrasound volume data including a lossy volume area where the ultrasound echo signal has a value equal to or less than a threshold value due to a strong reflector;

displaying a two dimensional (2D) rendered image of the face of the fetus and an ultrasound cross-sectional image of the face of the fetus, based on the ultrasound volume data, the 2D rendered image and the ultrasound cross-sectional image including a lossy area not represented of the face of the fetus due to the lossy volume area;

indicating, on the 2D rendered image, an area for restoration including the lossy area;

indicating, on the cross-sectional image, an area corresponding to the area for restoration indicated in the 2D rendered image; and restoring the indicated area for restoration indicated on the 2D rendered image based on a user input.

12. The method of claim 11, wherein the indicating of the area for restoration among the lossy area on the 2D rendered image and the cross-sectional image comprises determining the lossy volume area based on the ultrasound volume data and a direction in which the ultrasound signal is irradiated to the fetus;

determining the lossy area in the 2D rendered image and the ultrasound cross-sectional image based on the lossy volume area;

indicating the determined lossy area in the 2D rendered image and the ultrasound cross-sectional image as the area for restoration; and displaying a direction image representing the direction in which the ultrasound signal is irradiated to the fetus.

13. The method of claim 11, wherein the indicating of the area for restoration among the lossy area on the 2D rendered image and the cross-sectional image comprises receiving a user input to select an area for restoration on the displayed ultrasound cross-sectional image; and indicating an area selected on the ultrasound cross-sectional image and an area in the 2D rendered image corresponding to the selected area as the area for restoration.

14. The method of claim 11, wherein the indicating of the area for restoration among the lossy area on the 2D rendered image and the cross-sectional image comprises receiving a user input to select the area for restoration on the 2D rendered image of the face of the fetus; and indicating the selected area for restoration on the 2D rendered image.

15. The method of claim 11, further comprising:

displaying an image indicating a location of an eye of the fetus at the location of the eye of the fetus in the 2D rendered image; and clearly enhancing a shape of the eye of the fetus at the location of the eye of the fetus based on a user input to enhance the 2D rendered image of the face of the fetus being received.

16. The method of claim 15, wherein the displaying of the image indicating a location of an eye of the fetus at the location of the eye of the fetus in the 2D rendered image comprises determining a location of an eye of the fetus in the ultrasound volume data based on predetermined characteristics of the eye which appears in the ultrasound volume data; and determining a location on the 2D rendered image corresponding to the determined location of the eye of the fetus as a location of the eye of the fetus in the 2D rendered image.

17. The method of claim 15, wherein the displaying of the image indicating a location of an eye of the fetus at the location of the eye of the fetus in the 2D rendered image comprises receiving a user input to select an area of an eye of the fetus on the ultrasound cross-sectional image; and determining a location in the 2D rendered image corresponding to the selected area of the eye as a location of the eye of the fetus in the 2D rendered image.

18. The method of claim 15, wherein the displaying of the image indicating a location of an eye of the fetus at the location of the eye of the fetus in the 2D rendered image comprises receiving a user input to select a location of an eye of the fetus on the 2D rendered image of the face of the fetus.

19. The method of claim 11, further comprising:

displaying both the 2D rendered image including the lossy area and the restored 2D rendered image.

20. The method of claim 15, further comprising:

displaying a plurality of 2D rendered images on a sub-display of the ultrasound imaging apparatus, which have different enhancement levels and include the enhanced 2D rendered image; and based on a user input to select one of the plurality of 2D rendered images being received, displaying the selected 2D rendered image on a main display of the ultrasound imaging apparatus.

\* \* \* \* \*